United States Patent [19]  [11] 4,107,307
Paul et al.  [45] Aug. 15, 1978

[54] IMIDAZO [1,5-d]-AS-TRIAZINE-4(3H)-ONES AND THIONES

[75] Inventors: Rolf Paul, River Vale, N.J.; Judith Menschik, Tappan, N.Y.

[73] Assignee: American Cyanamid Company, Stamford, Conn.

[21] Appl. No.: 843,174

[22] Filed: Oct. 18, 1977

Related U.S. Application Data

[63] Continuation-in-part of Ser. No. 765,318, Feb. 3, 1977, abandoned.

[51] Int. Cl.$^2$ ............... A61K 31/53; C07D 253/08; C07D 487/04
[52] U.S. Cl. .................................. 424/249; 544/184; 71/93
[58] Field of Search .................... 544/184; 424/249

[56] References Cited

U.S. PATENT DOCUMENTS

| | | | |
|---|---|---|---|
| 2,837,520 | 6/1958 | Fusco et al. | 544/184 |
| 3,840,537 | 10/1974 | Garside et al. | 544/184 |

Primary Examiner—John M. Ford
Attorney, Agent, or Firm—Harry H. Kline

[57] ABSTRACT

There is provided substituted imidazo[1,5-d]-as-triazine-4(3H)-ones and substituted imidazo[1,5-d]-as-triazin-4(3H)-thiones useful as inhibitors of the enzyme cyclic-AMP phosphodiesterase and as broad spectrum herbicides.

27 Claims, No Drawings

IMIDAZO [1,5-d]-AS-TRIAZINE-4(3H)-ONES AND THIONES

This application is a continuation-in-part application of our copending application, Ser. No. 765,318, filed Feb. 3, 1977, now abandoned.

BRIEF SUMMARY OF THE INVENTION

This invention relates to new organic compounds and more particularly, is concerned with novel substituted imidazo[1,5-d]-as-triazin-4(3H)-ones and -thiones which may be represented by the following structural formula:

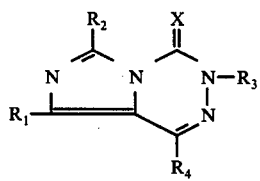

wherein X is divalent oxygen or divalent sulfur; $R_1$ is hydrogen, alkyl $C_1$–$C_3$, bromo, chloro, iodo or halo, alkyl $C_1$–$C_3$; $R_2$ is hydrogen, alkyl $C_1$–$C_6$, cycloalkyl $C_3$–$C_6$, methoxymethyl, benzyl, naphthyl, or phenyl optionally substituted with halogen, alkyl $C_1$–$C_4$, alkoxy $C_1$–$C_4$, halokyl $C_1$–$C_3$, amino, dialkylamino and nitro, $R_3$ is hydrogen, alkyl $C_1$–$C_3$, alkenyl $C_3$–$C_4$ or alkynyl $C_3$–$C_4$; and $R_4$ is hydrogen or alkyl $C_1$–$C_3$.

A preferred embodiment of the present invention may be represented by the above structural formula (I) wherein X is divalent oxygen; $R_1$ is methyl, bromo or chloro; $R_2$ is cycloalkyl $C_3$–$C_6$, phenyl or m-tolyl; and $R_3$ and $R_4$ are both hydrogen.

DETAILED DESCRIPTION OF THE INVENTION

The novel compounds of the present invention are generally obtainable as white to yellow crystalline materials having characteristic melting points and absorption spectra and which may be purified by recrystallization from common organic solvents such as methanol, ethanol, dimethylformamide chloroform, and the like. They are appreciably soluble in non-polar organic solvents such as diphenyl ether and carbon tetrachloride but are relatively insoluble in water.

The compounds (I) of the present invention wherein $R_3$ and $R_4$ are both hydrogen may be readily prepared in accordance with the following reaction scheme:

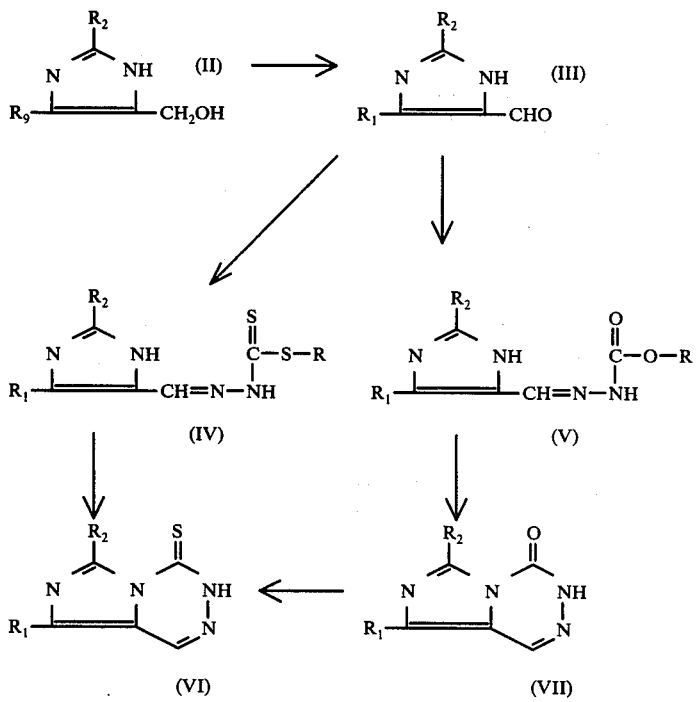

wherein R is methyl or ethyl, $R_1$ is hydrogen or alkyl having up to 3 carbon atoms, and $R_2$ is as hereinabove defined. In accordance with the above reaction scheme, an appropriately substituted 4-imidazolemethanol (II) is oxidized with concentrated nitric acid to provide the corresponding 4-imidazolecarboxaldehyde (III). This oxidation is best carried out by suspending or dissolving each gram of starting material (II) in from about 1 ml. to about 7 ml. of concentrated nitric acid and heating the reaction mixture at steam bath temperature for 2–3 hours. Alternatively, the reaction mixture may first be allowed to stand at room temperature for 8–16 hours and then heated for a short time (15–30 minutes) on the steam bath. The resulting reaction solution is preferably first diluted with water and then neutralized with any convenient base such as caustic, soda ash, or concentrated aqueous ammonia. The precipitated product (III) is removed, washed with water, and purified by recrystallization from common organic solvents such as ethyl acetate, ethanol, and the like. Alternatively, the 4-imidazolemethanol (II) may be oxidized with activated manganese dioxide in chloroform or tetrahydrofuran from room temperature to reflux temperatures for a period of 4–6 hours to provide the 4-imidazolecarboxaldehyde (III).

The 4-imidazolecarboxaldehyde (III) may be readily converted to the 3-(4-imidazolylmethylene)dithiocarbazic acid ester (IV) or the 3-(4-imidazolylmethylene)-carbazic acid ester (V) by treatment with methyl or ethyl dithiocarbazinate or with methyl or ethyl carbazate, respectively. This condensation is conveniently carried out in a lower alkanol solvent containing a few drops of glacial acetic acid at a temperature of 25°–75° C. whereupon the product (IV) or (V) forms almost immediately and is removed by filtration. Cyclization of the 3-(4-imidazolylmethylene)dithiocarbazic acid ester (IV) and the 3-(4-imidazolylmethylene)carbazic acid ester (V) is readily accomplished by heating in a non-polar high boiling organic solvent such as diphenyl ether at 175°–275° C. for 15–30 minutes whereby the corresponding imidazo[1,5-d]-as-triazine-4(3H)-thiones (VI) and imidazo[1,5-d]-as-triazin-4(3H)-ones (VII) are obtained.

The compounds (VII) wherein $R_1$ is chloro or bromo may be prepared by the chlorination or bromination, respectively, of the corresponding compounds (VII) wherein $R_1$ is hydrogen. This halogenation is accomplished by treating the starting materials with chlorine or bromine in an inert solvent such as chloroform or carbon tetrachloride at steam bath temperature. The oxo compounds (VII) can be converted to the thio compounds (VI) by treating with phosphorus pentasulfide in an inert solvent such as pyridine at the reflux temperature. This is a particularly convenient method when $R_1$ is halogen.

The compounds (VII) wherein $R_1$ is iodo may be prepared as follows:

The aldehyde (III) wherein $R_1$ is hydrogen is converted to the dimethyl acetal in methanol/HCl. The dimethyl acetal is iodinated, and then hydrolyzed to yield the corresponding iodoaldehyde (IIIa):

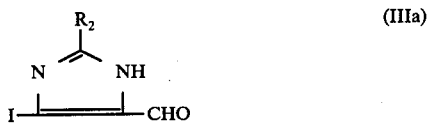

The thus-obtained iodoaldehyde (IIIa) is then converted by following the above-described route to the desired compound (VII) wherein $R_1$ is iodo.

Introduction of a $R_4$ substituent into the imidazo-as-trazinone ring may be accomplished by treatment of aldehyde (III) with alkyl($C_1$–$C_3$) magnesium bromide followed by a Jones oxidation. The latter method is described by Jones et al in J.C.S. 1946, 39 and in J.C.S. 1953, 457, 2548 and 3019. During oxidation of the secondary alcohol, a ketone (VIII) is obtained. These reactions are illustrated hereinbelow as follows:

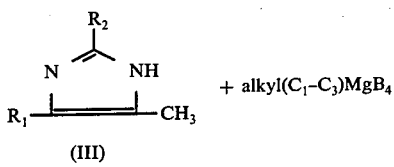

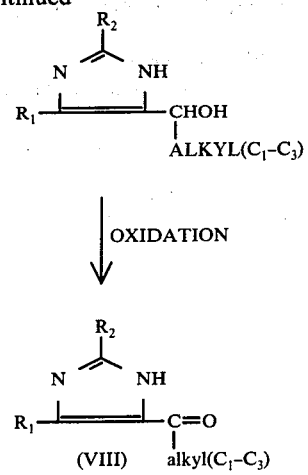

The remaining synthetic steps to the formula (I) product, wherein X is oxygen and $R_3$ is hydrogen, are accomplished by the above-described procedures via cyclization of the carbazic acid ester derivative of formula (VIII) ketone in either diphenyl ether or, preferably, o-dichlorobenzene.

Alkylation of formula (I) imidazo-as-triazone compounds ($R_3$ is hydrogen) at the 3-N-position is accomplished using conventional alkylating agents.

Another superior procedure for the 3-N-methylation of a specific imidazo-as triazinone, namely, 8-methyl-6-phenylimidazo[1,5-d]-as-triazin-4(3H)-one is the reaction of the latter triazinone with dimethyl formamide dimethyl acetal in an inert solvent, such as benzene or toluene, at a temperature of about 80°–90° C.

The novel compounds of the present invention are active as broad spectrum herbicides and in inhibiting the enzyme cyclic —AMP phosphodiesterase which is responsible for the metabolism of cyclic AMP. As such, they are useful in the treatment of psoriasis, a disease in which the epidermal cyclic AMP levels are reported to be decreased. Also as such they are useful in the treatment of asthma, since elevated levels of cyclic AMP in most cells are reported to inhibit the release of histamine and other mediators and since elevated levels of cyclic AMP in bronchial smooth muscle are reported to cause bronchodilation. See Ann. Reports in Medicinal Chem., Vol. 10, 197 (1975).

The inhibition of phosphodiesterase is determined by the mouse skin and monkey lung phosphodiesterase (PDE) inhibition tests as follows:

(A) MOUSE SKIN INHIBITION

Preparation of Mouse Skin PDE

Hairless mice (Jackson Laboratories), 3–4 months old are killed by cervical dislocation and their skins removed. Epidermal slices are taken at a thickness of 0.2 mm. The slices are weighed and homogenized at 100 mg./ml. in ice-cold tris-HCl buffer (0.04M, pH 8, containing 0.005M $MgCl_2$). Homogenates are centrifuged at 17,000 × gravity for 30 minutes. The supernatants are divided into aliquots which are stored at −20° C. Dilutions of the PDE are made with tris-HCl buffer just prior to use.

Anion Exchange Resin

AG1-X2 ®, 200–400 mesh (a polystyrene anionic exchange resin 8% cross linked from Bio-Rad Lab.) is washed with 0.5N HCl, 0.5N NaOH, 0.5N HCl and repeatedly with double distilled water to pH 5. The resin is allowed to settle and 2 volumes of water are added to one volume of settled resin.

Purification of $^3$H Cyclic AMP $^3$H-Cyclic AMP (21 c/m mole, Schwarz-Mann Inc.) is purified by addition of 0.1 to 0.2 ml. of stock (in 50% ethanol) to 5 ml. of anion exchange resin and 0.4 ml. of tris-HCl buffer. The mixture is vortexed, centrifuged at 1200 × gravity for 5 minutes and the supernatant is discarded. The resin is washed in the same manner eight more times with two volumes of tris-HCl buffer. Resin bound $^3$H-cyclic AMP is eluted by two successive washings with 4 ml. of 0.025N HCl (resin pH = 2.0). After centrifugation, the pooled acid washes containing $^3$H-cyclic AMP are aliquoted and lyophilized. The material is stored dry at −20° C. and reconstituted with tris-HCl buffer just prior to use with a volume sufficient to give approximately 200,000 CPM/0.1 ml.

PDE Assay

PDE activity is measured by the method of W. J. Thompson and N. N. Appleman, Biochemistry 10, 311 (1971). Assays are conducted in 12 × 75 mm. polypropylene test tubes. The reaction mixture consists of $^3$H-cyclic AMP (200,000 CPM) unlabeled cyclic AMP, PDE (100 ug. protein) and test compound which are prepared by dissolving the compounds in methanol at a concentration of 10 mg./ml. and then dilution in tris-HCl buffer. Final concentration of the test compounds in the incubation mixture is 10 ug./ml. The total volume of the incubation mixture is increased to 0.4 ml. with tris-HCl buffer containing 3.75 millimoles of 2-mercaptoethanol. The enzyme is incubated for 10 minutes at room temperature in the presence of the test compounds or buffer prior to the addition of the mixture of $^3$H-cyclic AMP and unlabeled cyclic AMP. Reactions are run at 30° C. for 15 minutes and then terminated by immersing in acetone-dry ice until frozen, followed by boiling for 3 minutes. Tubes are cooled to room temperature. $^3$H-5′ AMP, formed in the reaction is converted to $^3$H-adenosine by the addition of 0.1 ml. of a solution of 5′-nucleotidase [16 ug./ml. in double distilled water Crotalus venom (Sigma Chemicals)] to the tubes which are incubated for 20 minutes at room temperature. This reaction is ended by the addition of one ml. of ice cold, stirred resin slurry which binds charged nucleotides (including $^3$H-cyclic AMP) but not $^3$H-adenosine. Tubes are vortexed and immersed in an ice bath for 15 minutes and then centrifuged at 1200 × gravity for 5 minutes. A 0.5 ml. portion is taken from each, placed in liquid scintillation vials with 10 ml. of Ready-Solv VI (Beckman Ind.) and counted for radio activity. Assay "blanks", determined with assay buffer substituted for PDE are less than 1% of total $^3$H-cyclic AMP added when $^3$H-cyclic AMP is purified as indicated.

(B) MONKEY LUNG INHIBITION

Preparation of Monkey Lung Cyclic AMP Phosphodiesterase

Lung parenchyma of African green monkeys is homogenized in a Waring blender and centrifuged at 40,000 × gravity for 20 minutes. The supernatant is brought to 70% saturation of ammonium sulfate, centrifuged and the pellet redissolved and dialysed, before aliquoting and storage at −20° C.

Assay of Monkey Lung Phosphodiesterase

Phosphodiesterase is assayed by the method of Thompson and Appleman, ibid. An assay tube contains a 0.4 ml. solution of the following: 45 mM tris-HCl buffer, pH 7.4, 6.25 MgCl$_2$, 0.1 mM dithioerythritol, $10^{-6}$M cyclic AMP, 0.1 uCi [$^3$H]-cyclic AMP, and test compound at the desired concentration (usually 1 mM or 0.1 mM). Compounds not readily soluble in water are dissolved at 40 times the desired concentration in methanol, and diluted 20 times with water. If the compound is not dissolved at this time, it is suspended by sonication before being diluted 1:2 into the assay tube. In this case the activity of the enzyme in the presence of the compound is compared to a solvent control (2.5% methanol), although the solvent alone has negligible effect. The reaction is initiated by addition of enzyme and proceeds at 25° C. for 20 minutes. It is terminated by incubation at 100° C. for 2 minutes. The tubes are cooled to 25° C., 0.8 ug of 5′-nucleotidase (Crotolu adamantus toxin) is added to each and the tubes incubated at 25° C. for 30 minutes. A 1 milliliter suspension of Bio-Rad Labs. AGIX8 (about 0.5 ml. of settled resin) is added, the tubes centrifuged at 900 × gravity for 10 minutes and an aliquot of supernatant removed for scintillation counting. The inhibition by the test compound is calculated as:

$$\% \text{ of control} = \frac{\text{'compound' - 'blank'}}{\text{'control' - 'blank'}}$$

where 'compound' is the cpm in the presence of compound, 'control' is the cpm in the absence of compound, and 'blank' is the cpm in the absence of enzyme. Since this assay require sequential hydrolysis of cyclic AMP to AMP (by phosphodiesterase) followed by hydrolysis of AMP to adenosine (by 5′-nucleotidase), a compound which profoundly inhibited nucleotidase would appear to inhibit phosphodiesterase. For this reason, control tubes which contained [$^3$H]-AMP instead of [$^3$H]-cyclic AMP are run in parallel. A correction of the apparent phosphodiesterase activity is made for the rare compound which inhibited the hydrolysis of AMP.

Criterion for Activity as Inhibitor of Skin Phosphodiesterase

A compound is considered active if it inhibits more than theophylline, that is, to 50% of control at 1 mM concentration of compound, or to 80% of control of 0.05 mM concentration of compound.

The results with typical compounds of the present invention on inhibition of phosphodiesterase are recorded in Table I below.

TABLE I

| Compound | Mouse Lung Phosphodiesterase (B) | Mouse Skin Phosphodiesterase (A) |
|---|---|---|
| 6-Propyl-imidazo[1,5-d]-as-triazine-4(3H)-thione | Active | Active |

TABLE I-continued

| Compound | Mouse Lung Phosphodiesterase (B) | Mouse Skin Phosphodiesterase (A) |
| --- | --- | --- |
| 8-Methyl-6-phenyl-imidazo[1,5-d]-as-triazine-4(3H)-thione | | Active |
| 6-Phenyl-imidazo[1,5-d]-as-triazin-4-(3H)-one | | Active |
| 8-Methyl-6-phenyl-imidazo[1,5-d]-as-triazin-4(3H)-one | Active | Active |
| 6-Propyl-imidazo[1,5-d]-as-triazin-4(3H)-one | | Active |
| 6,8-Dimethyl-imidazo[1,5-d]-as-triazin-4(3H)-one | Active | Active |
| 8-Bromo-6-phenyl-imidazo[1,5-d]-as-triazin-4(3H)-one | Active | Active |
| 8-Chloro-6-phenyl-imidazo[1,5-d]-as-triazin-4(3H)-one | Active | Active |
| 6-Benzyl-8-methyl-imidazo[1,5-d]-as-triazin-4(3H)-one | | Active |
| 6-tert-Butyl-8-methyl-imidazo[1,5-d]-as-triazin-4(3H)-one | Active | Active |
| 6-Benzyl-8-methyl-imidazo[1,5-d]-as-triazin-4(3H)-thione | Active | Active |
| 8-Methyl-6-propyl-imidazo[1,5-d]-as-triazin-4(3H)-thione | Active | Active |
| 8-Methyl-imidazo[1,5-d]-as-triazine-4(3H)-thione | | Active |
| 6-o-Propoxyphenyl-imidazo[1,5-d]-as-triazin-4(3H)-one | | Active |
| 6-Benzyl-imidazo[1,5-d]-as-triazin-4(3H)-one | | Active |
| 6-tert-Butyl-imidazo[1,5-d]-as-triazin-4(3H)-one | | Active |
| 8-Methyl-imidazo[1,5-d]-as-triazin-4(3H)-one | | Active |
| 6,8-Dimethyl-imidazo[1,5-d]-as-triazin-4(3H)-thione | | Active |

Some of the novel compounds of the present invention possess anti-hypertensive activity at non-toxic doses and as such are useful as hypotensive agents. These compounds have been tested pharmacologically and found to have such properties with a desirable wide spread between doses producing lowered blood pressure and toxic symptoms. In determining this effect of these compounds on hypertension, adult male, 16–20 weeks old, spontaneous hypertensive rats from Taconic Farms, Germantown, N.Y., weighing about 300 grams are used. The rats are dosed by gavage with the test compounds at the indicated dose. All doses of drug were suspended in 2% starch (2 ml./kg.). A second identical dose of the test compound is given at the 24th hour. The mean arterial blood pressure (MAP) of the conscious rats is measured directly by femoral artery puncture at the 28th hour. The results of this test on these compounds appear in Table II below.

TABLE II

| Compound | Dose mg/kg | MAP (mm Hg) 28th hour |
| --- | --- | --- |
| Imidazo[1,5-d]-as-triazin-4(3H)-thione | 100 | 123 |
| 8-Methyl-imidazo[1,5-d]-as-triazine-4(3H)-thione | 25 | 130 |
| 6-Propyl-imidazo[1,5-d]-as-triazine-4(3H)-thione | 100 | 136 |
| 8-Methyl-6-phenyl-imidazo[1,5-d]-as-triazine-4(3H)-thione | 100 | 128 |
| 6-Phenyl-imidazo[1,5-d]-as-triazin-4(3H)-one | 100 | 117 |
| 8-Methyl-6-phenyl-imidazo[1,5-d]-as-triazin-4(3H)-one | 100 | 133 |
| 6,8-Dimethyl-imidazo-[1,5-d]-as-triazin-4(3H)-one | 50 | 70 |
| 6-tert-Butyl-imidazo-[1,5-d]-as-triazin-4(3H)-one | 100 | 135 |
| 6-Methyl-imidazo[1,5-d]-as-triazin-4(3H)-one | 100 | 120 |
| 8-Methyl-imidazo[1,5-d]-as-triazin-4(3H)-one | 100 | 91 |
| 6-tert-Butyl-8-methyl-imidazo[1,5-d]-as-triazin-4(3H)-one | 100 | 133 |
| 6,8-Dimethyl-imidazo-[1,5-d]-as-triazine-4(3H)-thione | 100 | 93 |
| 8-Methyl-6-propyl-imidazo[1,5-d]-as-triazin-4(3H)-one | 50 | 127 |
| 6-Methoxymethyl-imidazo-[1,5-d]-as-triazine-4(3H)-thione | 100 | 100 |
| Controls | vehicle | 166 |

The novel compounds of the present invention have thus been found to be highly useful for meliorating asthma and for inhibiting diesterase in mammals when administered in amounts ranging from about 1.0 migram to about 100.0 mg. per kilogram of body weight per day. A preferred dosage regimen for optimum results would be from about 5.0 mg. to about 50.0 mg. per kilogram of body weight per day, and such dosage units are employed that a total of from about 0.35 gram to about 3.5 gram of active compound for a subject of about 70 kg. of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compounds may be administered in any convenient manner such as by the oral, intravenous, intramuscular, or subcutaneous routes and also by inhalation therapy including aerosol sprays.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl- -glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate.

Generally, from about 0.05 to about 2.0% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 250 and 500 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the ike; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantialy non-toxic in the amounts employed.

The invention will be described in greater detail in conjunction with the following specific examples.

EXAMPLE 1

5-Methyl-2-phenyl-4-imidazolemethanol

A 100 gm. portion of benzamidine hydrochloride is dissolved in a minimum of water (350 ml.) at room temperature. A 67 gm. portion of freshly distilled 2,3-butanedione is added giving a yellow solution. Adjusting the pH to 6–7 with 2N NaOH gives a solid which is allowed to stand at 0° C. for 2 hours, collected, pressed dry and then washed with 100 ml. of acetone. This material is heated with stirring on a steam bath with 855 ml. of concentrated HCl and 2437 ml. of water for 4 hours giving a solution. Cooling to room temperature overnight and then to 0° C. produces a solid which is collected and air dried. This solid is dissolved in 350 ml. of ethanol, filtered and cooled producing a gel, which is taken up in 250 ml. of 50°–60° C. water, adjusted to pH 5.5 with concentrated NaOH and then to pH 7–8 with solid KHCO$_3$. The mixture is cooled to 0° C. and the product is collected, washed with water, and air dried. This product is recrystallized from 1 liter of methanol giving the final product, m.p. 197°–199° C.

Alternatively, this product may be prepared by the method of Imbach et al., Bull. Soc. Chim. France, 1971, 1052.

EXAMPLE 2

2-Phenyl-4-imidazolomethanol

This product is prepared by the methods of Dziuron and Schunack, Arch. Pharm., 306, 347 (1973) and 307, 46 (1974).

EXAMPLE 3

2-n-Propyl-4-imidazolemethanol

A mixture of 180 gm. of 1,3-dihydroxyacetone dimer, 245 gm. of butyramidine hydrochloride and 1 liter of liquid ammonia are warmed to 60° C. for 5 hours in a bomb. The mixture is evaporated to dryness and the residue is stirred with 600 ml. of 2-propanol. The mixture is filtered and the filtrate is concentrated in vacuo. A 600 ml. portion of 50% saturated aqueous sodium carbonate is added and the mixture is extracted with three 150 ml. portions of tetrahydrofuran. The combined organic layers are washed with 330 ml. of saturated aqueous sodium carbonate. The organic layer is dried over anhydrous sodium sulfate and evaporated to dryness. The residue is twice recrystallized from acetone giving the product, m.p 95°–101° C.

EXAMPLE 4

2,5-Dimethyl-4-imidazolemethanol hydrochloride

This product is prepared by the method of Imbach et al., Bull. Soc. Chim. France, 1971, 1052.

EXAMPLE 5

2-Methyl-4-imidazolemethanol

A 189 gm. portion of acetamidine hydrochloride and 180 gm. of 1,3-dihydroxyacetone are combined with 1 liter of liquid ammonia as described in Example 3, giving the desired product, m.p. 115°–117.5° C.

EXAMPLE 6

4,5-Dimethyl-2-n-propyl-2-imidazoline-4,5-diol hydrochloride

A 112.7 gm. portion of butyramidine hydrochloride is dissolved in 200 ml. of water. A 107 gm. portion of freshly distilled diacetyl is added and the mixture is stirred. The pH is adjusted to 6.5–7.0 with 2N NaOH and the solution is chilled. The desired product is collected as a solid, m.p. 104°–107° C.

EXAMPLE 7

5-Methyl-2-n-propyl-4-imidazolemethanol

The product from Example 6 is dissolved in 900 ml. of water and 350 ml. of concentrated hydrochloric acid, heated on a steam bath for 5 hours and then chilled. The solution is concentrated in vacuo and a mixture of 100 ml. of acetone and 100 ml. of ethanol is added. The mixture is filtered. The filtrate is evaporated and the residue is dissolved in 50 ml. of water and neutralized with a concentrated solution of $K_2CO_3$, until bubbling ceases. The top layer is separated and combined with 5 ml. of methanol. On standing, a precipitate forms. The solid is collected and the filtrate is diluted with acetone to give a second precipitate which is also collected. The solids are combined and recrystallized from hot acetone giving the desired product, m.p. 134°–136° C.

EXAMPLE 8

5-Methyl-4-imidazolemethanol

This product is prepared by the method of Ewins, J. Chem. Soc. 99, 2052 (1911).

EXAMPLE 9

2-(o-Propoxyphenyl)-4-imidazolemethanol

A 130 gm. portion of salicylamide in 500 ml. of ethanol is reacted with 52.4 gm. of sodium methoxide and 164.9 gm. of 1-iodopropane by heating at reflux. The mixture is cooled, precipitated in 1500 ml. of water and the solid is recrystallized from hot ethanol giving o-propoxybenzamide.

A 109 gm. portion of the above compound in 500 ml. of chloroform is reacted with 49.4 ml. of methyl fluorosulfonate by refluxing for 3 hours. After cooling, the mixture is concentrated to an oil. Ether is added forming crystals which are recovered, giving o-propoxy benzimidic acid methyl ester fluorosulfate.

A 180 gm. portion of this latter product and 55.0 gm. of 1,3-dihydroxyacetone in one liter of liquid ammonia are reacted as in Example 3, giving the desired product, m.p. 90°–92° C.

EXAMPLE 10

2-Benzyl-4-imidazolemethanol

A 352 gm. portion of benzyl cyanide, 750 ml. of diethyl ether and 300 ml. of dry ethanol are placed in a 2 liter, three-necked flask with a magnetic stirrer, drying tube and quick-disconnect gas inlet. The mixture is stirred in an ice bath while hydrochloride gas is bubbled in for 1 hour. The mixture is placed in a chill room overnight. One liter of ether is added and the mixture is cooled. The precipitate is collected and washed with ether giving ethyliminophenylacetate hydrochloride.

A 272 gm. portion of the above compound and 126 gm. of 1,3-dihydroxyacetone in 1 liter of liquid ammonia are reacted as in Example 3 giving the desired product, m.p. 134°–135° C.

EXAMPLE 11

2-Methoxymethyl-4-imidazolemethanol

A 307.2 gm. portion of ethyl 2-methoxyacetimidate hydrochloride [Rule, J. Chem. Soc. 113, 9 (1918)] and 180 gm. of 1,3-dihydroxyacetone in 1 liter of liquid ammonia are reacted as described in Example 3 giving the desired product as an oil. A crystalline picrate salt (m.p. 175°–178° C.) is obtained by heating the oily product and picric acid in water.

EXAMPLE 12

2-tert-Butyl-4-imidazolemethanol

A mixture of 326 gm. of pivalimidic acid methyl ester hydrochloride and 193.5 gm. of 1,3-dihydroxyacetone in 2 liters of liquid ammonia are reacted as described in Example 3, giving the desired product, m.p. 212°–221° C.

EXAMPLE 13

2-tert-Butyl-5-methyl-4-imidazolemethanol

In a 2 liter, three-necked flask, equipped with a magnetic stirrer, drying tube and gas inlet tube, is put 200 gm. of trimethylacetonitrile, 250 ml. of methanol and 500 ml. of diethyl ether. Hydrochloride gas is bubbled in for 2 hours with stirring. The mixture is transferred to a beaker, ether is added and the beaker is covered and stored in a cold room overnight. A 500 ml. portion of ether is added and the solid is filtered and washed with ether, giving white crystals of pivalimidic acid methyl ester hydrochloride.

A 75 gm. portion of the above material is converted to methyl pivalimidate hydrochloride by the method of Brown and Evans, J. Chem. Soc. 1962, 4039.

A 61 gm. portion of this latter product is dissolved in 50 ml. of water with warming and then cooled to room temperature. A 38.3 gm. portion of freshly distilled diacetyl is added and the reaction is continued as described in Examples 6 and 7 giving the desired product as white crystals, m.p. 195.5°–196.5° C.

EXAMPLE 14

2-Benzyl-5-methyl-4-imidazolemethanol

To a solution of 109.6 gm. of α-phenylacetamidine hydrochloride [Luckenback, Chem. Ber. 17, 1423 (1884)] in 50 ml. of water is added 55.4 gm. of freshly distilled diacetyl. The mixture is stirred, the precipitate is collected, triturated in portions with 200 ml. of acetone and air dried, giving 2-benzyl-4,5-dimethyl-4,5-dihydroxyimidazolidine.

A mixture of 106 gm. of this latter product, 170 ml. of concentrated hydrochloride and 170 ml. of water is reacted as described in Example 7 giving the desired product, m.p. 134°–138° C.

EXAMPLE 15

2-Phenyl-4-imidazolecarboxaldehyde

A 17.4 gm. portion of 2-phenyl-4-imidazolemethanol and 13.4 ml. of concentrated $HNO_3$ are heated on a steam bath for 2½ hours. Three drops of fuming $HNO_3$ are added to start the reaction. The pH is adjusted to 8 with concentrated aqueous $Na_2CO_3$ and the mixture is cooled to 0° C. overnight. The solid is recovered, washed with water and recrystallized from a mixture of 70 ml. of ethyl acetate and 20 ml. of petroleum ether giving a yellow solid. Treatment of the mother liquor with petroleum ether gives an additional tacky substance which is triturated with isopropanol giving a second solid. These two solids are taken up in hot isopropanol and recrystallized as a yellow solid. This solid is recrystallized from ethanol:water (1:1) giving yellow crystals, m.p. 169°–171.5° C.

EXAMPLE 16

2-n-Propyl-4-imidazolecarboxaldehyde

A solution of 108.6 gm. of 2-n-propyl-4-imidazolemethanol in 107 ml. of concentrated $HNO_3$ is reacted as in Example 15, giving the desired product, m.p. 103.5°–105.5° C.

EXAMPLE 17

2-n-Butyl-4-imidazolecarboxaldehyde

Following the general procedure of Example 15, 2-n-butyl-4-imidazolemethanol is converted to 2-n-butyl-4-imidazolecarboxaldehyde.

EXAMPLE 18

5-Methyl-2-phenyl-4-imidazolecarboxaldehyde

A 102.1 gm. portion of 5-methyl-2-phenyl-4-imidazolemethanol is dissolved in 765 ml. of concentrated $HNO_3$. The solution is cooled in an ice bath and allowed to stand for 16 hours. The solution is heated on a steam bath for 30 minutes, diluted with 2.3 liters of water and neutralized with 50% NaOH while cooling in an ice bath. The solid is collected, dried, recrystallized from 200 ml. of ethanol and then from 1 liter of 1:2 ethanol:water giving the desired product, m.p. 102°–115° C.

Alternatively, this product may be prepared by the method of Diels and Schleich, Chem. Ber. 49, 1711 (1916).

EXAMPLE 19

5-Ethyl-2-phenyl-4-imidazolecarboxaldehyde

The procedure of Example 18 is repeated substituting an equimolecular amount of 5-ethyl-2-phenyl-4-imidazolemethanol for the 5-methyl-2-phenyl-4-imidazolemethanol employed in that example. There is thus obtained the title compound in equally good yield.

EXAMPLE 20

2,5-Dimethyl-4-imidazolecarboxaldehyde

A 42.2 gm. portion of 2,5-dimethyl-4-imidazolemethanol and 44.8 ml. of concentrated nitric acid are mixed. When the initial reaction subsides, the solution is heated on a steam bath for 1 hour. The reaction mixture is neutralized with concentrated aqueous sodium carbonate, then concentrated under vacuum. After leaching the residue with 150 ml. of hot ethanol several times, the combined organic solutions are concentrated under vacuum. Chromatographing the residual oil on silica gel gives a solid which is recrystallized from isopropanol-ethyl acetate to give the desired product, m.p. 164.5°–166° C.

EXAMPLE 21

5-Methyl-4-imidazolecarboxaldehyde

This product is prepared by the method of Hubball and Pyman, J. Chem. Soc. 1928, 21.

EXAMPLE 22

2-o-Propoxyphenyl-4-imidazolecarboxaldehyde

A 44 gm. portion of 2-(o-propoxyphenyl)-4-imidazolemethanol is placed in a 2 liter round bottom flask together with 500 ml. of chloroform and 100 gm. of manganese dioxide. The mixture is stirred and refluxed for 5½ hours. The reaction mixture is filtered while hot. The manganese dioxide is triturated with 500 ml. of hot chloroform and filtered. The two filtrates are combined and evaporated. The solid residue is recrystallized from 200 ml. of hot ethyl acetate and charcoal giving the desired product, m.p. 104°–105° C.

EXAMPLE 23

2-Methyl-4-imidazolecarboxaldehyde

A 143.0 ml. portion of concentrated $HNO_3$ is added in two portions to 119.2 gm. of 2-methyl-4-imidazolemethanol, with cooling after the first portion, and reacted as described in Example 15, giving the desired product, m.p. 170°–176° C.

Alternatively, this product may be made by the methods of Streith et al., Bull. Soc. Chim. France, 4159 (1971) and also Abushanab et al., J. Org. Chem. 40, 3376 (1975).

EXAMPLE 24

2-Benzyl-4-imidazolecarboxaldehyde

A 125 gm. portion of 2-benzyl-4-imidazolemethanol and 500 g. of manganese dioxide in 2 liters of chloroform are reacted as described in Example 22 giving the desired product, m.p. 130°–136° C.

EXAMPLE 25

2-(Methoxymethyl)-4-imidazolecarboxaldehyde

A 145.9 gm. portion of 2-methoxymethyl-4-imidazolemethanol and 137 ml. of concentrated $HNO_3$ are reacted as described in Example 15. After adjusting the pH to 7.0 with concentrated aqueous $Na_2CO_3$, the solution is concentrated under vacuum. Extraction of the residue three times with hot ethanol gives, after combining and concentrating the extracts, a yellow gum. This gum is chromatographed on silica gel. Fractions 7–15 are combined and recrystallized from 120 ml. of isopropanol, treated with charcoal and the desired product is recovered, m.p. 100°–103° C.

EXAMPLE 26

2-Benzyl-5-methyl-4-imidazolecarboxaldehyde

A mixture of 8.79 gm. of 2-benzyl-5-methyl-4-imidazolemethanol and 55.7 ml. of concentrated $HNO_3$ is left at room temperature overnight. The solution is heated for 45 minutes on a steam bath, cooled, the basified with aqueous sodium carbonate. After heating the resulting mixture on a steam bath, it is cooled and the solid collected. Two recrystallizations from ethanol give the desired product, m.p. 171°–173° C.

EXAMPLE 27

2-Benzyl-5-n-propyl-4-imidazolecarboxaldehyde

The general procedure of Example 26 is repeated but replacing the 2-benzyl-5-methyl-4-imidazolemethanol employed in that example with 2-benzyl-5-n-propyl-4-imidazolemethanol.

EXAMPLE 28

5-Methyl-2-n-propyl-4-imidazolecarboxaldehyde

An 80 gm. portion of 5-methyl-2-n-propyl-4-imidazolemethanol is oxidized with 67.3 ml. of concentrated $HNO_3$. A second portion of 101.4 gm. of the above compound is oxidized with 77 ml. of the acid. The reaction mixtures are combined, neutralized and worked up as in Example 25, giving the desired product, m.p. 126°–129° C.

EXAMPLE 29

2-tert-Butyl-4-imidazolecarboxaldehyde

A 7.7 gm. portion of 2-tert-butyl-4-imidazolemethanol is added to 100 ml. of chloroform and 100 ml. of tetrahydrofuran and heated gently. A 25 gm. portion of manganese dioxide is added and the mixture is reacted as described in Example 22 giving the desired product as white crystals, m.p. 194°–195° C.

EXAMPLE 30

2-tert-Butyl-5-methyl-4-imidazolecarboxaldehyde

A 19.76 gm. portion of 2-tert-butyl-5-methyl-4-imidazolemethanol and 16.5 ml. of concentrated HNO$_3$ are reacted as described in Example 25 giving the desired product, m.p. 196°–198° C.

EXAMPLE 31

2-Isobutyl-5-isopropyl-4-imidazolecarboxaldehyde

The procedure of Example 30 is repeated substituting an equimolecular amount of 2-isobutyl-5-isopropyl-4-imidazolemethanol for the 2-tert-butyl-5-methyl-4-imidazolemethanol employed in that example. There is thus obtained the title compound in equally good yield.

EXAMPLE 32

3-(4-imidazolylmethylene)dithiocarbazic acid methyl ester

A 17.78 gm. portion of imidazole-4-carboxaldehyde (Pyman, J. Chem. Soc. 1916, 186) is dissolved in 200 ml. of hot ethanol. A hot solution of 24.4 gm. of methyl dithiocarbazinate [Audrieth et al., J. Org. Chem. 19, 733 (1954)] in 50 ml. of ethanol is added. A precipitate forms immediately and the mixture is heated and stirred for about 10 minutes. The mixture is cooled to 0° C. The precipitate is collected giving yellow crystals, m.p. 259°–261° C.

EXAMPLE 33

3-(2-Phenyl-4-imidazolylmethylene)dithiocarbazic acid methyl ester

A 35 gm. portion of 2-phenyl-4-imidazolecarboxaldehyde is taken up in 250 ml. of hot ethanol. A solution of 22.8 gm. of methyl dithiocarbazinate in 40 ml. of hot ethanol is added and the procedure of Example 32 is followed giving the desired product, m.p. 166°–170° C.

EXAMPLE 34

3-[(5-Methyl-2-phenyl-4-imidazolyl)methylene]dithiocarbazic acid methyl ester A 60 gm. portion of 5-methyl-2-phenyl-4-imidazolecarboxaldehyde and 36.8 gm. of methyl dithiocarbazinate are reacted as described in Example 32 giving the desired product, m.p. 180°–185° C.

EXAMPLE 35

3-[(5-Ethyl-2-phenyl-4-imidazolyl)methylene]dithiocarbazic acid methyl ester Following the general procedure of Example 34, 5-ethyl-2-phenyl4-imidazolecarboxaldehyde is converted to 3-[(5-ethyl-2-phenyl-4-imidazolyl)methylene]-dithiocarbazic acid methyl ester.

EXAMPLE 36

3-(2-n-Propyl-4-imidazolylmethylene)dithiocarbazic acid methyl ester

A 60 gm. portion of 2-n-propyl-4-imidazolecarboxaldehyde and 53.7 gm. of methyl dithiocarbazinate are reacted as described in Example 32 giving the desired product, m.p. 95°–104° C.

EXAMPLE 37

3-(2-Methyl-4-imidazolyl-methylene(dithiocarbazic acid methyl ester

A 33 gm. portion of 2-methyl-4-imidazolecarboxaldehyde and 40.3 gm. of methyl dithiocarbazinate are reacted as described in Example 32 giving the desired product, m.p. 274°–279° C.

EXAMPLE 38

3-(5-Methyl-4-imidazolylmethylene)dithiocarbazic acid methyl ester

A 16 gm. portion of 5-methyl-4-imidazolecarboxaldehyde and 19.5 gm. of methyl dithlocarbazinate are reacted as described in Example 32 giving the desired product, m.p. 180° d resolidifies 230°–260° C.

EXAMPLE 39

3-[(2,5-Dimethyl-4-imidazolyl)methylene]dithiocarbazic acid methyl ester

A 20 gm. portion of 2,5-dimethyl-4-imidazolecarboxaldehyde and 20.8 gm. of methyl dithiocarbazinate are reacted as described in Example 32 giving the desired product, m.p. 279°–281° C.

EXAMPLE 40

3-{[2-(Methoxymethyl)-4-imidazolyl]methylene}dithiocarbazic acid methyl ester A 40 gm. portion of 2-(methoxymethyl)-4-imidazolecarboxaldehyde and 38.4 gm. of methyl dithiocarbzinate are reacted as described in Example 32 giving the desired product, m.p. 150°–154° C.

EXAMPLE 41

3-[(5-Methyl-2-n-propyl-4-imidazolyl)methylene]dithiocarbacid methyl ester

A 20 gm. portion of 5-methyl-2-n-propyl-4-imidazolecarboxaldehyde and 17.7 gm. of methyl dithiocarbazinate are reacted as described in Example 32 giving the desired product, m.p. 175°–179° C.

EXAMPLE 41

3-[(2-benzyl-5-n-Propyl-4-imidazolyl)methylene]dithiocarbazic acid methyl ester The general procedure of Example 41 is repeated but replacing the 5-methyl-2-n-propyl-4-imidazolecarboxaldehyde employed in that example with 2-benzyl-5-n-propyl-4-imidazolecarboxaldehyde.

EXAMPLE 43

3-[(2,5-Dimethyl-4-imidazolyl)methylene]carbazic acid ethyl ester

A 6.2 gm. portion of 2,5-dimethyl-4-imidazolecarboxaldehyde and 6.24 gm. of ethyl carbazate are reacted as described in Example 32 giving the desired product, m.p. 207.5°– 210° C. (resolidifies 248°–252° C.).

EXAMPLE 44

3-(2-n-Propyl-4-imidazolylmethylene)carbazic acid ethyl ester

A 7.8 gm. portion of 2-n-propyl-4-imidazolecarboxaldehyde and 6.24 gm. of ethyl carbazate is reacted as described in Example 32 giving the desired product, m.p. 180°–182° C.

EXAMPLE 45

3-(2-Phenyl-4-imidazolylmethylene)carbazic acid ethyl ester

A mixture of 8.16 gm. of 2-phenyl-4-imidazolecarboxaldehyde and 5.52 gm. of ethyl carbazate are reacted as described in Example 32 giving the desired product, m.p. 196°–200° C.

EXAMPLE 46

3-[(5-Methyl-2-phenyl-4-imidazolyl)methylene]carbazic acid ethyl ester

A mixture of 10.25 gm. of 5-methyl-2-phenyl-4-imidazolecarboxaldehyde and 5.72 gm. of ethyl carbazate in 30 ml. of ethanol containing one drop of acetic acid is boiled for 30 minutes. The mixture is cooled to 0° C. and concentrated under an air stream on a steam bath. A 50 ml. portion of carbon tetrachloride is added and the mixture is cooled to 0° C. overnight. The solid is collected giving the desired product, m.p. 209°–211° C.

EXAMPLE 47

3-[(2-o-Propoxyphenyl-4-imidazolyl)methylene]carbazic acid ethyl ester

A 4.3 gm. portion of 2-o-propoxyphenyl-4-imidazolecarboxaldehyde and 1.98 gm. of ethyl carbazate are reacted as described in Example 32 giving the desired product, m.p. 129°–132°C.

EXAMPLE 48

3-[(2-Benzyl-4-imidazolyl)methylene]carbazic acid ethyl ester

To a 37.2 gm. portion of 2-benzyl-4-imidazolecarboxaldehyde in 200 ml. of ethanol is added 20.8 gm. of ethyl carbazate and a few drops of concentrated acetic acid. The mixture is reacted as described in Example 32 giving the desired product m.p. 184°–185° C.

EXAMPLE 49

3-(2-tert-Butyl-4-imidazolylmethylene)carbazic acid ethyl ester

A 7.6 gm. portion of 2-tert-butyl-4-imidazolecarboxaldehyde and 5.2 gm. of ethyl carbazate in 100 ml. of ethanol are reacted as described in Example 32 giving the desired product, m.p. 194°–197° C.

EXAMPLE 50

3-(2-n-Butyl-4-imidazolylmethylene) carbazic acid ethyl ester

The procedure of Example 49 is repeated substituting an equimolecular amount of 2-n-butyl-4-imidazolecarboxaldehyde for the 2-tert-butyl-4-imidazolecarboxaldehyde employed in that example. There is thus obtained the title compound in equally good yield.

EXAMPLE 51

3-(2-Methyl-4-imidazolylmethylene) carbazic acid ethyl ester

A solution of 16.68 gm. of ethyl carbazate in 50 ml. of hot ethanol is added to a solution of 16.50 gm. of 2-methyl-4-imidazolecarboxaldehyde in 100 ml. of hot ethanol containing 2 drops of acetic acid. The reaction is carried out as described in Example 32 giving the desired product, m.p. 210.5°–211.5° C.

EXAMPLE 52

3-(5-Methyl-4-imidazolylmethylene) carbazic acid ethyl ester

A mixture of 7.0 gm. of 5-methyl-4-imidazolecarboxaldehyde and 7.3 gm. of ethyl carbazate are reacted as described in Example 32 giving the desired product, m.p. 195°–203° C.

EXAMPLE 53

3-[2-(Methoxymethyl)-4-imidazolyl]methylene carbazic acid ethyl ester

A 19.60 gm. portion of 2-(methoxymethyl)-4-imidazolecarboxaldehyde and 16.02 gm. of ethyl carbazate are reacted as described in Example 32 giving the desired product, m.p. 186°–190° C.

EXAMPLE 54

3-[(2-Benzyl-5-methyl-4-imidazolyl)methylene]carbazic acid ethyl ester

A 4.08 gm. portion of 2-benzyl-5-methyl-4-imidazolecarboxaldehyde and 2.29 gm. of ethyl carbazate are reacted as described in Example 32 giving the desired product, m.p. 190°–191.5° C.

EXAMPLE 55

3-[(2-tert-Butyl-5-methyl-4-imidazolyl)methylene]carbazic acid ethyl ester

A 6.17 gm. portion of 2-tert-butyl-5-methyl-4-imidazolecarboxaldehyde and 4.20 gm. of ethyl carbazate are reacted as described in Example 32 giving the desired product, m.p. 226°–228.5° C.

EXAMPLE 56

3-[(2-Isobutyl-5-isopropyl-4-imidazolyl)methylene]carbazic acid ethyl ester

Following the general procedure of Example 55, 2-isobutyl-5-isopropyl-4-imidazolecarboxaldehyde is converted to the title compound in equally good yield.

EXAMPLE 57

3-[(5-Methyl-2-n-propyl-4-imidazolyl)methylene]carbazic acid ethyl ester

A 12 gm. portion of 5-methyl-2-n-propyl-4-imidazolecarboxaldehyde and 9.06 gm. of ethyl carbazate are reacted as described in Example 32 giving the desired product, m.p. 184°–188° C.

EXAMPLE 58

Imidazo[1,5-d]-as-triazine-4(3H)-thione

A suspension of 164.5 gm. of 3-(4-imidazolylmethylene)dithiocarbazic acid methyl ester in 1.2 liters of diphenyl ether is heated and stirred at 175° C. until the methylmercaptan evolution subsides (20 minutes). The precipitate obtained on cooling to room temperature is collected and washed with petroleum ether, then acetone. The precipitate is then slurried with 1.2 liters of boiling methanol and filtered while hot to give the desired product, m.p. 271°–273° C.

EXAMPLE 59

8-Methyl-imidazo[1,5-d]-as-triazine-4-(3H)-thione

A suspension of 14.39 gm. of 3-(5-methyl-4-imidazolylmethylene)dithiocarbazic acid methyl ester in 100 ml. of diphenyl ether is reacted as described in Example 58 giving the desired product as yellow crystals, m.p. 262°–268° C.

EXAMPLE 60

6-Phenyl-imidazo[1,5-d]-as-triazine-4(3-H)-thione

A suspension of 7.05 gm. of 3-(2-phenyl-4-imidazolyl-methylene)dithiocarbazic acid methyl ester in 100 ml. of diphenyl ether is reacted as described in Example 58 giving the desired product, m.p. 210° C.

EXAMPLE 61

6-n-Propyl-imidazo[1,5-d]-as-triazine-4(3H)-thione

A 102.2 gm. portion of 3-(2-n-propyl-4-imidazolylmethylene)dithiocarbazic acid methyl ester in 500 ml. of diphenyl ether is reacted as described in Example 58 giving the desired product as a white solid, m.p. 201.5°–203.5° C.

EXAMPLE 62

8-Methyl-6-phenyl-imidazo[1,5-d]-as-triazine-4-(3H)-thione

A mixture of 73.4 gm. of 3-[(5-methyl-2-phenyl-4-imidazolyl)methylene]dithiocarbazic acid methyl ester and 500 ml. of diphenyl ether is reacted as described in Example 58 giving the desired product as purple crystals, m.p. 237.5°–239° C.

EXAMPLE 63

8-Ethyl-6-phenyl-imidazo[1,5-d]-as-triazine-4(3H)-thione

The general procedure of Example 62 is repeated but replacing the 3-[(5-methyl-2-phenyl-4-imidazolyl)methylene]-dithiocarbazic acid methyl ester employed in that example with 3-[(5-ethyl-2-phenyl-4-imidazolyl)-methylene]dithiocarbazic acid methyl ester.

EXAMPLE 64

6,8-Dimethyl-imidazo[1,5-d]-as-triazine-4-(3H)-thione

A mixture of 30.26 gm. of 3-[(2,5-dimethyl-4-imidazolyl)methylene]dithicarbazic acid methyl ester and 125 ml. of diphenyl ether is reacted as described in Example 58 giving a solid which is the desired product, m.p. 287.5°–290° C.

EXAMPLE 65

6-Benzyl-8-methyl-imidazo[1,5-d]-as-triazine-4(3H)-thione

A 2.04 gm. portion of 2-benzyl-5-methyl-4-imidazolecarboxaldehyde is dissolved in 20 ml. of ethanol containing 2 drops of acetic acid. A 1.34 gm. portion of methyldithiocarbazinate is added, the mixture is boiled for 30 minutes and then cooled to 0° C. overnight. The mixture is evaporated giving 3-[(2-benzyl-5-methylimidazolyl)methylene]dithiocarbazic acid methyl ester as an oil.

A 3.40 gm. portion of the above product is dissolved in 30 ml. of diphenyl ether and heated for 9 minutes at 194°–207° C. The mixture is cooled to room temperature and diluted with hexane. The solid is recrystallized from 150 ml. of methanol and treated with charcoal giving the desired product, m.p. 207°–209.5° C.

EXAMPLE 66

6-Benzyl-8-n-propyl-imidazo[1,5-d]-as-triazine-4-(3H)-thione

The procedure of Example 65 is repeated substituting an equimolecular amount of 3-[(2-benzyl-5-n-propylimidazolyl)-methylene]dithiocarbazic acid methyl ester for the 3-[(2-benzyl-5-methylimidazolyl)-methylene]dithiocarbazic acid methyl ester employed in that example. There is thus obtained the title compound in equally good yield.

EXAMPLE 67

8-Methyl-6-n-propyl-imidazolo[1,5-d]-as-triazine-4(3H)-thione

A mixture of 32.12 gm. of 3-[(5-methyl-2-n-propyl-4-imidazolyl)methylene]dithiocarbazic acid methyl ester and 200 ml. of diphenyl ether is reacted as described in Example 58 giving the desired product, m.p. 183°–186° C.

EXAMPLE 68

6-Methyl-imidazo[1,5-d]-as-triazine-4(3H)-thione

A mixture of 53.9 gm. of 3-(2-methyl-4-imidazolyl-methylene)dithiocarbazic acid methyl ester and 200 ml. of diphenyl ether is reacted as described in Example 58 giving the desired product, m.p. 280.5°–284° C.

EXAMPLE 69

6-Methoxymethyl-imidazo[1,5-d]-as-triazine-4-(3H)-thione

A miture of 62.4 gm. of 3-[2-(methoxymethyl)-4-imidazolyl]methylene dithiocarbazic acid methyl ester and 250 ml. of diphenyl ether is reacted as described in Example 58 giving the desired product, m.p. 219.5°–223° C.

EXAMPLE 70

6-o-Propoxyphenyl-imidazo[1,5-d]-as-triazine-4(3H)-one

A 10.5 gm. portion of 3-[(2-o-propoxyphenyl-4-imidazolyl)methylene]carbazic acid ethyl ester in 100 ml. of diphenyl ether is heated on an oil bath with stirring at 255°–265° C. until effervesence subsides. The mixture is cooled to room temperature. The addition of petroleum ether produces a solid which is recrystallized from methanol with the aid of charcoal giving the desired product as a bright yellow solid, m.p. 197°–200° C.

EXAMPLE 71

6-Benzyl-imidazo[1,5-d]-as-triazin-4(3H)-one

A 7.0 gm. portion of 3-[(2-benzyl-4-imidazolyl)me-thylene]carbazic acid ethyl ester in 50 ml. of diphenyl ether is reacted as described in Example 70 giving the desired product as white crystals, m.p. 215°–217° C.

EXAMPLE 72

6-Phenyl-imidazo[1,5-d]-as-triazin-4(3H)-one

A 7.76 gm. portion of 3-(2-phenyl-4-imidazolylmethylene)carbazic acid ethyl ester in 50 ml. of diphenyl ether is reacted as described in Example 70 giving the desired product m.p. 245°–248° C.

EXAMPLE 73

8-Methyl-6-phenyl-imidazo[1,5-d]-as-triazin-4(3H)-one

An 8.33 gm. portion of 3-[(5-methyl-2-phenyl-4-imidazolyl)methylene]carbazic acid ethyl ester in 60 ml. of diphenyl ether is heated in an oil bath at 25°–230° C. for 20 minutes. The reaction mixture is diluted to 400 ml. with petroleum ether. The precipitate is collected and recrystallized from 350 ml. of benzene giving the desired product, m.p. 182°–184.5° C.

EXAMPLE 74

6-n-Propyl-imidazo[1,5-d]-as-triazin-4(3H)-one

An 8.75 gm. portion of 3-(2-n-propyl-4-imidazolylmethylene)carbazic acid ethyl ester in 50 ml. of diphenyl ether is reacted as described in Example 70 giving the desired product, m.p. 159°–162.5° C.

EXAMPLE 75

6,8-Dimethyl-imidazo[1,5-d]-as-triazin-4(3H)-one

A mixture of 7.37 gm. of 3-[(2,5-dimethyl-4-imidazolyl)methylene]carbazic acid ethyl ester and 50 ml. of diphenyl ether is reacted as described in Example 70 giving the desired product, m.p. 263°–263.5° C.

EXAMPLE 76

6-tert-Butyl-imidazo[1,5-d]-as-triazin-4(3H)-one

A 6.15 gm. portion of 3-(2-tert-butyl-4-imidazolylmethylene)carbazic acid ethyl ester in 40 ml. of diphenyl ether is reacted as described in Example 70 giving the desired product, m.p. 186°–188° C.

EXAMPLE 77

6-n-Butyl-imidazo[1,5-d]-as-triazin-4(3H)-one

Following the general procedure of Example 76, 3-(2-n-butyl-4-imidazolylmethylene)carbazic acid ethyl ester is converted to the title compound.

EXAMPLE 78

6-Methyl-imidazo[1,5-d]-as-triazin-4(3H)-one

A 27.2 gm. portion of 3-(2-methyl-4-imidazolylmethylene)carbazic acid ethyl ester in 200 ml. of diphenyl ether is reacted as described in Example 70 giving the desired product m.p. 303°–305.5° C.

EXAMPLE 79

8-Methyl-imidazo[1,5-d]-as-triazin-4(3H)-one

A mixture of 10.26 gm. of 3-(5-methyl-4-imidazolylmethylene)carbazic acid ethyl ester and 100 ml. of diphenyl ether is reacted as described in Example 70 giving the desired product, m.p. 276°–282° C.

EXAMPLE 80

6-Benzyl-8-methyl-imidazo[1,5-d]-as-triazin-4(3H)-one

A mixture of 4.89 gm. of 3-[(2-benzyl-5-methyl-4-imidazolyl)methylene]carbazic acid ethyl ester and 50 ml. of diphenyl ether is reacted as described in Example 70 giving the desired product, m.p. 244°–247° C.

EXAMPLE 81

6-tert-Butyl-8-methyl-imidazo[1,5-d]-as-triazin-4(3H)-one

A mixture of 5.11 gm. of 3-[(2-tert-butyl-5-methyl-4-imidazolyl)methylene]carbazic acid ethyl ester and 50 ml. of diphenyl ether is reacted as described in Example 70 giving the desired product, m.p. 198°–200° C.

EXAMPLE 82

6-Isobutyl-8-isopropyl-imidazo[1,5-d]-as-triazin-4(3H)-one

The general procedure of Example 81 is repeated but replacing the 3-[(2-tert-butyl-5-methyl-4-imidazolyl)methylene]carbazic acid ethyl ester employed in that example with 3-[(2-isobutyl-5-isopropyl-4-imidazolyl)methylene]carbazic acid ethyl ester.

EXAMPLE 83

8-Methyl-6-n-propyl-imidazo[1,5-d]-as-triazin-4(3H)-one

A 14.50 gm. portion of 3-[(5-methyl-2-n-propyl-4-imidazolyl)methylene]carbazic acid ethyl ester and 100 ml. of diphenyl ether are reacted as described in Example 70 giving the desired product, m.p. 129.5°–131.5° C.

EXAMPLE 84

6-Methoxymethyl-imidazo[1,5-d]-as-triazin-4(3H)-one

A mixture of 25.9 gm. of 3-[2-(methoxymethyl)-4-imidazolyl]methylene carbazic acid ethyl ester and 125 ml. of diphenyl ether is reacted as described in Example 70 giving the desired product, m.p. 200°–205° C.

EXAMPLE 85

8-Bromo-6-phenyl-imidazo[1,5-d]-as-triazin-4(3H)-one

A 3.0 gm. portion of 6-phenyl-imidazo[15-d]-as-triazin-4(3H)-one is stirred with 100 ml. of chloroform. The mixture is heated slightly and a solution of 1 ml. of bromine in 10 ml. of chloroform is slowly dripped into the reaction mixture. The mixture is refluxed for 1 hour, cooled to room temperature, and filtered. To the solid is added aqueous $Na_2CO_3$ and chloroform and the mixture is shaken in a separatory funnel. The remaining solid and the organic phase are combined and evaporated on a steam bath. Methanol and 2-propanol are added and the mixture is treated twice with charcoal. Cooling gives the desired product as a solid, m.p. 192°–194° C.

EXAMPLE 86

8-Bromo-6-n-butyl-imidazo[1,5-d]-as-triazin-4(3H)-one

The procedure of Example 85 is repeated substituting an equimolecular amount of 6-n-butyl-imidazo[1,5-d]-as-triazin-4(3H)-one for the 6-phenyl-imidazo[1,5-d]-as-triazin-4(3H)-one employed in that example. There is thus obtained the title compound in equally good yield.

EXAMPLE 87

8-Chloro-6-phenyl-imidazo[1,5-d]-as-triazin-4(3H)-one

A 5.0 gm. portion of 6-phenyl-imidazo [1,5-d]-as-triazin-4(3H)-one is mixed with 100 ml. of chloroform on a stream bath while chlorine gas is bubbled through the mixture. A 25 ml. portion of methanol is added. Chlorine is again bubbled through for 10–15 minutes. The mixture is cooled to room temperature, transferred to a separatory funnel, washed with aqueous Na₂CO₃, aqueous NaHSO₃ and finally with water. The mixture is evaporated to 75 ml. of a steam bath, cooled and filtered. The filtrate is evaporated overnight giving a solid. This solid is dissolved in 30 ml. of hot chloroform and filtered. The filtrate is treated with charcoal and 2-propanol is added giving the desired product as a solid, m.p 201°–203° C.

EXAMPLE 88

8-Chloro-6-benzyl-imidazo[1,5-d]-as-triazin-4(3H)-one

Following the general procedure of Example 86, 6-benzyl-imidazo[1,5-d]-as-triazin-4(3H)-one is chlorinated to give the title compound.

EXAMPLE 89

8-Methyl-6-phenyl-imidazo[1,5-d]-as-triazine-4(3H)-thione

To a solution of 4.5 gm. of 8-methyl-6-phenyl-imidazo-[1,5-d]-as-triazin-4(3H)-one in 100 ml. of pyridine is added 5 gm. of phosphorus pentasulfide. The reaction mixture is heated at 100° C. for 8 hours, filtered, and poured into dilute hydrochloric acid. The precipitated product is isolated by filtration, washed with water, and dried.

EXAMPLE 90

8-Bromo-6-phenyl-imidazo[1,5-d]-as-triazine-4(3H)-thione

The procedure of Example 89 is repeated but substituting an equimolar amount of 8-bromo-6-phenyl-imidazo [1,5-d]-as-triazin-4(3H)-one for the 8-methyl-6-phenyl-imidaz [1,5-d]-as-triazin-4(3H)-one employed in that example.

EXAMPLE 91

8-Chloro-6-phenyl-imidazo[1,5-d]-as-triazin-4(3H)-one

The use of 5-chloro-2-phenyl-4-imidazolecarboxaldehyde and ethyl carbazate in the procedure of Example 46 afford 3-[(5-chloro-2-phenyl-4-imidazolyl)methylene]-carbazic acid ethyl ester, which is converted to the title compound by heating in diphenyl ether as in Example 70

EXAMPLE 92

5-Methyl-2-m-tolyl-4-imidazolemethanol

A mixture of cis and trans-4,5-dimethyl-2-m-tolyl-2-imidazoline-4,5-diol hydrochloride (9.0 g, 0.035 mole) and 3N hydrochloric acid (135 ml) is stirred and heated on a steam bath for 2.5 hours and then stirred at 0–5° for 0.75 hours. The reaction mixture is filtered to yield 7.4 g (0.031 mole) of a white solid. The solid is treated with base to afford the title compound, m.p. 190°–192° C (d).

Analysis calculated for C₁₂H₁₄N₂O; C, 71.26; H, 6.98; N, 13.85; Found: C, 70.94; H, 7.07; N, 13.92.

Additional imidazolemethanol compounds prepared by the above procedure are listed in Table III below.

Table III

| $R_2$ | m.p.(C°) | Analysis Calculated | Found |
|---|---|---|---|
|  | 215–216(d) | C 56.65<br>H 4.75<br>N 18.02 | C 56.64<br>H 4.73<br>N 17.74 |
|  | >150(d) | C 71.26<br>H 6.98<br>N 13.85 | C 70.86<br>H 6.97<br>N 13.60 |
|  | 111–114 | | |
|  | 205–207 | C 66.04<br>H 6.47<br>N 12.83 | C 65.75<br>H 6.88<br>N 12.90 |
|  | 132–134(d) | | |
|  | 205–207(d) | C 59.33<br>H 4.98<br>N 12.58 | C 59.73<br>H 5.22<br>N 12.44 |
|  | >170(d) | C 59.33<br>H 5.09<br>N 10.11 | C 59.73<br>H 5.18<br>N 9.86 |
|  | 175–177 | | |
|  | 188–190(d) | | |
|  | >120(d) | | |
| C₄H₉— | syrup | | |
| C₆H₁₃— | syrup | | |
|  | 104–106(d) | | |
|  | 115–120(d) | | |
|  | 182–183(d) | C 68.00<br>H 9.34<br>N 14.42 | C 67.73<br>H 9.55<br>N 13.87 |

EXAMPLE 93

Preparation of 2-substituted 5-methyl-4-imidazolecarboxhydes

Method A

5-Methyl-2-mtolyl-4-imidazolecarboxaldehyde

A mixture of 5-methyl-2-mtolyl-4-imidazolemethanol (13.0 g, 0.064 mole), activated manganese dioxide (65g) and methylene chloride (200 ml) is stirred at room temperature for 20 hours. The reaction mixture is then filtered, the solvent removed in vacuo to afford 9.1 g (0.045 mole) of peach-colored solid.

Method B 5-methyl-2-(p-nitrophenyl)-4-imidazolecarboxaldehyde

A mixture of 5-methyl-2-(p-nitrophenyl)-4-imidazole methanol (2.9 g, 0.012 mole) and 70% nitric acid (20 ml) is stirred at 50° C for 3 hours, followed by dilution with water and neutralization with base. The precipitated yellow solid is collected by filtration to yield 2.4 g (0.011 mole) of title product, dec >270° C.

Analysis calculated for C₁₁H₉N₃O₃: C, 57.14; H, 3.92; N, 18.17; Found: C, 56.69; H, 3.96; N, 18.08.

METHOD C

Preparation of 2-alkyl(cycloalkyl)-5-methylimidazole-4-carboxaldehydes

A mixture of 2-alkyl(cycloalkyl)-5-methyl-4-imidazolemethanol (0.1 mole), activated manganese dioxide (0.5 mole) and chloroform (500 ml) is stirred and refluxed for 2 hours, then stirred overnight (appx. 15–16 hours) at room temperature. The mixture is filtered through a bed of filter-aid, the solution evaporated to dryness and the residue recrystallized from the appropriate solvent.

By one or the other methods of preparation, a number of 2-substituted 5-methyl-4-imidazolecarboxaldehydes are made. The compounds, their method of preparation, melting points and analytical data are given in Table IV below.

Table IV

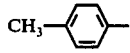

| $R_2$ | Method* | m.p.(C°) | Analysis Calculated | Found |
|---|---|---|---|---|
| 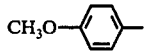 CH$_3$— | A | 142–194(d) | N 13.99 | N 14.28 |
| 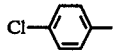 CH$_3$O— | A | 161–163(d) | C 66.65<br>H 5.89<br>N 12.95 | C 66.52<br>H 5.86<br>N 13.08 |
| 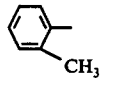 Cl— | A | 237–239(d) | C 59.88<br>H 4.11<br>N 12.70 | C 59.30<br>H 4.17<br>N 12.61 |
| 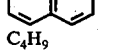 CH$_3$ | A | 140–143(d) | C 71.98<br>H 6.04<br>N 13.99 | C 71.61<br>H 6.37<br>N 13.87 |
|  | A | 197–199(d) | C 76.25<br>H 5.12<br>N 11.86 | C 76.15<br>H 5.25<br>N 11.81 |
| C$_4$H$_9$ | A | 83–84 | C 65.03<br>H 8.49<br>N 16.85 | C 64.85<br>H 7.96<br>N 17.04 |
| C$_6$H$_{15}$ | A | syrup | C 65.00<br>H 9.42<br>N 13.79 | C 65.72<br>H 9.15<br>N 13.64 |
|  | A | 104–109 | | |
|  | A | 114–130 | | |
| (cyclohexyl) | A | 159–162 | C 68.72<br>H 8.39<br>N 14.57 | C 69.06<br>H 8.44<br>N 14.43 |

*Preferred solvent in chloroform. p-dioxane and tert-butanol are also used.

EXAMPLE 94

α-Methyl-2-phenyl-4-imidazolemathanol

Methyl magnesium to bromide (15.3 ml, 2.5 molar in ether) is added dropwise to a solution of 2-Phenyl-4-imidazolecarboxaldehyde (3.0 g, 0.017 mole) in dry tetrahydrofuran (45 ml; dried over a molecular sieve) while the temperature of the reaction mixture is maintained with cooling at 25° C. The mixture is stirred for 2 hours and then decomposed by adding a large volume of water dropwise. The mixture is extracted with ether (3 × 75), the ethereal extract is partially evaporated to yield a white precipitate, the crystalline alcohol, m.p. 197°–198° C.

Analysis calculated for C$_{11}$H$_{12}$N$_2$O: C, 70.19; H, 6.43; N, 14.88; Found: C, 70.10; H, 6.68; N, 14.90.

EXAMPLE 95

α,5-dimethyl-2-phenyl-4-imidazolemethanol

α,5-Dimethyl-2-phenyl-4-imidazolemethanol is prepared from 5-methyl-2-phenyl-4-imidazolecarboxaldehyde (37.0 g, 0.199 mole) by the method of Example 94. The product (38.4 g, 95.5%) is obtained as a white crystalline solid, m.p. 189°–190° C.

EXAMPLE 96

Preparation of methyl 2-phenyl-4-imidazolyl ketone

Jones reagent [5 ml; a solution of chromium trioxide (10.3 g) is a mixture of sulfunic acid (8.7 ml) and water (30 ml)] is added at 0°–5° C over 1 hour to a solution of methyl-2-phenyl-4-imidazolemethanol (3.0 g, 0.016 mole) in acetone (25 ml). The temperature is allowed to rise to 20° C for 30 minutes then water (150 ml) is added. The mixture is stirred for 1 hour and the precipitated solid collected by filtration. The solid is treated with 2N hydrochloric acid (15 ml), stirred 5 minutes, and is then neutralized with 10% sodium hydroxide. The aqueous mixture is extracted with methylene chloride (3 × 75 ml). Removal of the methylene chloride yields the ketone as a white crystalline solid (1.73 g), m.p. 158°–158.5° C.

Analysis calculated for C$_{11}$H$_{12}$N$_2$O: C, 70.95; H, 5.41; N, 15.04; Found: C, 70.34; H, 5.52; N, 15.08.

EXAMPLE 97

Preparation of methyl-5-methyl-2-phenyl-4-imidazolyl ketone

By the method of Example 96, methyl-5-methyl-2-phenyl-4-imidazolyl ketone is prepared from α,5-dimethyl-2-phenyl-4-imidazolemethanol (12.0g, 0.059 mole). The product is obtained as a pale yellow crystalline solid (6.88 g, 58.3%), m.p. 188°–190° C.

Analysis calculated for C$_{12}$H$_{12}$N$_2$O: C, 71.98; H, 6.04; N, 13.99; Found: C, 71.30; H, 6.29; N, 13.40.

EXAMPLE 98

Preparation of 2-phenyl-5-imidazolecarboxaldehyde dimethyl acetal

A solution of 2-phenyl-5-imidazolecarboxaldehyde (6.10 g, 0.035 mole) in methanol (200 ml) is cooled in an ice bath and then saturated with hydrogen chloride. The reaction mixture is stirred overnight (appx. 15–16 hrs.) and added slowly to cold 6N sodium hydroxide (200 ml). The solution is neutralized with concentrated hydrochloric acid and the precipitated solid collected by filtration (7.56 g; 0.035 mole). Recrystallization from chloroform yields white needles, m.p. 158°–160° C.

Analysis calculated for C$_{12}$H$_{14}$N$_2$O$_2$: C, 66.03; H, 6.48; N, 12.83; Found: C, 65.38; H, 7.01; N, 12.63.

EXAMPLE 99

Preparation of 4-iodo-2-phenyl-5-imidazolecarboxaldehyde dimethyl acetal, and 4-iodo-2-phenyl-5-imidazolecarboxaldehyde A solution of iodine (10.25, g, 0.0404 mole) in methanol (200 ml) is added with stirring to a solution of 2-phenyl-5-imidazolecarboxaldehyde dimethyl acetal (7.56 g, 0.035 mole) is methanol (200 ml), water (20 ml) and 6N sodium hydroxide (13 ml). The reaction mixture is stirred for 5 hours, and then concentrated in vacuo to about 75 ml volume. Water (200 ml) is added and the precipitated 4-iodo2-phenyl-5-imidazolecarboxaldehyde dimethyl acetal (2.82 g, 0.0082 mole) is collected by filtration, m.p. 144°–148.5° C(d).

The aqueous filtrate is acidified with concentrated hydrochloric acid and the precipitated 4-iodo-2-phenyl-5-imidazolecarboxaldehyde (5.51 g. 0.018 mole) is collected by filtration, m.p. 208°–210° C(d).

Recrystallization of 4-iodo-2-phenyl-5-imidazolecarboxaldehyde dimethyl acetal from methyl cyclohexane. The yields white crystals, m.p. 152°–153.5° C.
Analysis calculated for $C_{12}H_{13}N_2O_2I$: C, 41.88; H, 3.82; N, 8.14; Found: C, 41.82; H, 4.19; N, 8.34.

Recrystallization of 4-iodo-2-phenyl-5-imidazolecarboxaldehyde from ethyl acetate yields a white solid, m.p. 211.5°–212.5° C.
Analysis calculated for $C_{10}H_7N_2OI$: C, 40.29; H, 2.37; N, 9.39; Found: C, 40.19; H, 2.37; N, 9.34.

EXAMPLE 100

Method for the preparation of 3-[(2-substituted-5-methyl4-imidazolyl)methylane]carbazic acid methyl ester

A.
3-[(5-methyl-2-m-tolyl-4-imidazolyl)methylene]-carbazic acid, methyl ester.

A mixture of 5-methyl-2-m-tolyl-4-imidazolecarboxaldehyde (6.9 g, 0.034 mole), methyl carbazate (3.1 g, 0.034 mole). methylene chloride (70 ml) and acetic acid (1 drop) is refluxed for 1 hour. The precipitated white solid is collected by filtration to yield 7.1 g (0.026 mole), mp. 162°–164° c.

By the above procedure, several 2 -aryl analogs of the above compound are prepared. These compounds, their melting points and analyses are listed in Table V below.

B. Preparation of 3-[(2-alkyl or cycloalkyl-5-methyl-4-imidazolyl)methylene]carbazic acid, methyl esters

A mixture of 2-alkyl(cycloalkyl)-5-methylimidazole-4-carboxaldehyde (0.1 mole), methyl carbazate (0.1 mole), toluene (60 ml) and acetic acid (0.5 ml) is refluxed for 2 hours. The reaction mixture is then cooled down, the solids are collected by filtration, and are recrystallized from the appropriate solvent.

The 2-alkyl and cycloalkyl compounds prepared by the above procedure are listed in Table V below.

Table V

| | | | Analysis | |
|---|---|---|---|---|
| $R_2$ | $R_1$ | m.p.(° C) | Calculated | Found |
| O$_2$N—⟨phenyl⟩— | CH$_3$— | 264–265(d) | C 51.49<br>H 4.32<br>N 23.09 | C 50.96<br>H 4.33<br>N 23.31 |
| CH$_6$—⟨phenyl⟩— | CH$_3$— | 226–227(d) | | |
| CH$_3$O—⟨phenyl⟩— | CH$_3$— | 176–178(d) | C 58.32<br>H 5.59<br>N 19.43 | C 58.01<br>H 5.60<br>N 19.23 |
| Cl—⟨phenyl⟩— | CH$_3$— | 234–235(d) | C 53.34<br>H 4.48<br>N 19.14 | C 52.95<br>H 4.42<br>N 18.99 |
| ⟨o-tolyl, CH$_3$⟩ | CH$_3$— | 160–162(d) | | |

Table V-continued

Structure: imidazole with N-H, $R_2$, $R_1$ substituents and —CH=N—NH—CO$_2$CH$_3$

| | | | Analysis | |
|---|---|---|---|---|
| $R_2$ | $R_1$ | m.p.(° C) | Calculated | Found |
| ⟨naphthyl⟩ | CH$_3$— | >170(d) | | |
| C$_4$H$_9$— | CH$_3$— | 189.5–190.5(d) | C 55.44<br>H 7.61<br>N 23.52 | C 55.09<br>H 7.71<br>N 23.54 |
| C$_6$H$_{13}$— | CH$_3$— | 164–165(d) | C 58.62<br>H 8.33<br>N 21.04 | C 58.34<br>H 7.78<br>N 20.83 |
| ⟨cyclopropyl⟩ | CH$_3$— | 184–186(d) | C 54.04<br>H 6.35<br>N 25.21 | C 54.25<br>H 6.49<br>N 25.33 |
| ⟨cyclobutyl⟩ | CH$_3$— | 196–197(d) | | |
| ⟨cyclohexyl⟩ | CH$_3$— | 193–194(d) | C 59.07<br>H 7.63<br>N 21.20 | C 58.62<br>H 7.61<br>N 20.80 |
| Cl—⟨phenyl⟩— · H$_2$O | Cl | 147–148 | C 43.5<br>H 3.63<br>N 16.9 | C 45.04<br>H 3.05<br>N 16.09 |

EXAMPLE 101

Preparation of 3-[1-(5-iodo-2-phenyl-4-imidazolyl)ethylidene]carbazic acid, methyl ester A solution of 4-iodo-2-phenyl-5-imidazolecarboxaldehyde (5.21 g, 0.017 mole) in a mixture of methanol (50 ml), toluene (250 ml), aceytic acid (1 ml) and methyl carbazatc (1.73 g, 0.019 mole) is refluxed for 24.5 hours. The solution is then heated for an additional hour, allowing solvent (100 ml) to distill off. The remaining solvent is then received in vacuo. The solids are extracted with methylene chloride (300 ml), and the extract washed with water (3 × 200 ml). At this point the product crystallizes and is collected by filtration (2.16 g, 0.0056 mole). Evaporation of the filtrate yields additional product (3.44 g, 0.0093 mole). Recrystallization from methanol-methylene chloride yields white crystals, m.p. 145°–147° C(d).

EXAMPLE 102

Preparation of 3-[5-methyl-2-phenyl-4-imidazolyl)ethylidene[-carazic acid, methyl ester Methyl 5-methyl-2-phenyl-4-imidazolyl ketone (4.5 g, 0.023 mole) is refluxed with methyl carbazatc (2.4 g, 0.023 mole) in toluene (112 ml) for 5 hours. The toluene is removed, and the solid washed with water (3 × 50 ml). The solid is recrystallized from methanol to yield the product (1.28 g, 20.9%), m.p. 201°–201° C.
Analysis calculated for $C_{14}H_{16}N_4O_2$: C, 61.75; H, 5.92; N, 20.57; Found: C, 60.05; H, 6.25; N, 19.96.

EXAMPLE 103

Preparation of 3-[1-(2-phenyl-4-imidazolyl)ethylidene]carbazic acid, methyl ester.

By the method of Example 102, the title product is prepared from methyl 2-phenyl-4-imidazolyl ketone and methyl carbazate. The product is obtained in 91% yield, m.p. 226.5°–227° C.

Analysis calculated for $C_{13}H_{14}N_4O_2$: C, 60.46; H, 5.46; N, 21.69; Found: C, 60.59; H, 5.60; N, 21.89.

EXAMPLE 104
Preparation of 6-(Aryl)-8-methyl-imidazo[1,5-d]-as-triazin-4(3H)-ones.

Method A

8 Methyl-6-m-tolyl-imidazo[1,5-d]-as-triazine-4(3H)-one.

A mixture of 3-[(5-methyl-2-m-tolyl-4-imidazolyl)-methylene]carbazic acid, methyl ester (5.1 g, 0.019 mole) and o-dichlorobezene (75 ml) is heated slowly (45 minutes) to reflux, refluxed for 1.5 hours, then stirred at room temperature over night (appr. 15–16 hours). The reaction mixture is filtered to afford 3.9 g (0.016 mole) title product. Recrystallization from o-dichlorobenzene yields partially solvated product, m.p. 188°–198° C.

By substituting 3{[5-methyl)-2-(α,α,α-trifluoro-m-tolyl)-4-imidazolyl]methylene}carbazic acid, methyl ester for 3-[(5-methyl-2-m-tolyl-4-imidazolyl)methylene]carbazic acid, methyl ester in the above reaction, 8-methyl-6-(α,α,α-trifluror-m-tolyl)-imidazo[1,5-α]-as-triazine-4(3H)-one can be obtained.

Method B

8-Methyl-6-(p-nitrophenyl)-imidazo[1,5-d]-as-triazine-4(3H)-one, monohydrate

3-{[2-(p-nitrophenyl)-5-methyl-4-imidazolyl]-methylene}carbazic acid, methyl ester (2.5 g, 0.0082 mole) is immersed in diphenyl ether (25 ml) at 240° C for 20 minutes, then stirred in an ice bath for 1 hour. The reaction mixture is diluted with ether and filtered to afford 2.2 g (0.008 mole) title product. The product is purified via an acetone soxhlet extraction to give a yellow solid, m.p. 295°–297° C.

Analysis calculated for $C_{12}H_{11}N_5O_4$: C, 49.83; H, 3.83; N, 24.21; Found: C, 49.69; H, 3.71; N, 23.88.

Method C

Preparation of 6-alkyl(cycloalkyl)-8-methylimidazo-[1,5-d]as-triazin-4(3H)-ones

The above compounds are prepared by Method A excepting that the mixture of Z-alkyl(cycloalkyl)-5-methylimidazole-4-carboxalolehyde methyl carbazone and odichlorobenzene is heated until a boiling point of 180° C is obtained. The solvent is removed by evaporation and the residue recrystallized from the appropriate solvents.

The compounds prepared by Method A, B and C, their melting points and analyses are listed in Table VI below.

TABLE VI

| $R_1$ | $R_2$ | $R_4$ | Method | m.p.(° C) | Analysis Calculated | Found |
|---|---|---|---|---|---|---|
| $CH_3$— | $CH_3$—⟨phenyl⟩— | H | A | 169–171.5(α) | | |
| $CH_3$— | $CH_3O$—⟨phenyl⟩— | H | A | 216–217(α) | C 60.93<br>H 4.72<br>N 21.86 | C60.52<br>H 4.80<br>N 21.70 |
| $CH_3$— | Cl—⟨phenyl⟩— | H | A | <240(α) | | |
| $CH_3$— | ⟨o-tolyl⟩ $CH_3$ | H | A | 185–191 | | |
| $CH_3$— | ⟨naphthyl⟩ | H | A | 247–251(α) | | |
| Cl— | Cl—⟨phenyl⟩— | H | A | 245–246(α) | C 47.00<br>H 2.15<br>N 19.93 | C 47.72<br>H 2.41<br>N 19.57 |
| H | ⟨phenyl⟩ | $CH_3$— | A | 281–281.8 | | |
| $CH_3$ | ⟨phenyl⟩ | $CH_3$— | A | 207–212 | | |
| $CH_3$ | $C_4H_9$— | H | C | 118–120 | C 58.23<br>H 6.84<br>N 27.17 | C 58.16<br>H 6.84<br>N 27.14 |
| H<br>$C_6H_3$— | H | | C | 118–119  H 7.74 | C 61.51<br>H 7.61 | C 61.28 |
| H | ▷ | | C | 210.5–211.5 | N 23.91<br>C 56.83<br>H 5.30<br>N 29.46 | N 23.68<br>C 56.65<br>H 5.64<br>N 29.43 |

TABLE VI-continued

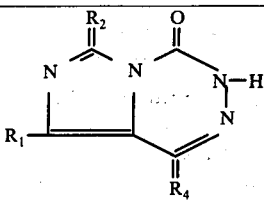

| R$_1$ | R$_2$ | R$_4$ | Method | m.p.(° C) | Analysis Calculated | Found |
|---|---|---|---|---|---|---|
| H |  | H | C | 179–181 | | |
| H |  | H | C | 145–147 | C 64.94<br>H 7.78<br>N 21.15 | C 63.38<br>H 8.10<br>N 20.41 |

EXAMPLE 105

Preparation of
6-Phenyl-8-iodo-imidazo[1,5-d[-as-triazin-4(3H)-one

3-[1-(5-Iodo-2-phenyl-4-imidazolyl)alkylidene]carbazic acid methyl ester (1.01 g, 0.0027 mole) is dissolved in a mixture of o-dichlorobenzene (150 ml) and methanol (15 ml). The solution is heated to the boiling point and boiled for 20 minutes allowing solvent to distill off partially. The reaction mixture is chromatographed over a silica gel column and eluted with hexane-ethyl acetate (2:1) mixture to yield the title product (0.63 g, 0.0019 mole). Recrystallization from ethyl acetate-hexane hyields the product as yellow meedles, m.p. 170°–189° C.

EXAMPLE 106

Preparation of
6-(p-anilino)-8-methyl-imidazo[1,5-d]-astrazin-4(3H)-one

Catalytic reduction of 8-methyl-6-(p-nitrophenyl)-imidazo[1,5-d]-as-triazin-4(3H)-one, monohydrate (1.3g, 0.0048 mole) in dimethylformamide (50 ml) with hhydrogen in the presence of 10% Pa/C catalyst and at atmospheric pressure followed by solvent removal in vacuo, affords the product (1.0 g, 0.0043 mole). Crystallization from dimethylformamide water yields a mustard-yellow solid, m.p. 252°–254° C($\alpha$).

EXAMPLE 107

Preparation of
8-Bromo-6-(m-anilino)imidazo-[1,5-(d)]-as-triazin-4(3H)-one

A mixture of 8-bromo-6-(m-nitrophenyl)imidazo-[1,5-d]-as-triazin-4(3H)-one (2.0 g, 0.00595 mole) and catalyst (Ru/C, 5%, 700 mg) are blanketed with nitrogen at atmospheric pressure and dimethylformamide (45 ml) is added. The flask containing the above mixture is vigorously shaken while hydrogen is introduced and absorbed (399 ml, 0.01785 mole). The catalyst is then filtered and washed with dimethylformamide. The filtrate is evaporated in vacuo. The product is recrystallized from diethyl ether, m.p. 205° C($\alpha$).

EXAMPLE 108

Preparation of
8-Bromo-6-(m-dimethylaminophenyl)-imidazo-[1,5-d]-as-triazin-4(3H)-one Sodium cyanoborogydride (1.2 g, 0.019 mole) is added to a stirred solution of 8-bromo-6-(m-amino-phenyl)imidazo-[1,5-d]-as-triazine-4(3H)-one, aqueous formaldehyde (5 ml, 37%) in acetonitrile (110 ml). The reaction mixture is stirred for 15 minutes then acetic acid is added to adjust the pH of the reaction mixture to 7. The reaction mixture is stirred for 45 minutes while the pH of the mixture is maintained at 7 with acetic acid being added as needed. The solvent is then evaporated in vacuo, the residual oil is added to 2N potassium hydroxide (150 ml), and crystallized. The product is washed with water, and recrystallized from acetone-water, m.p. 206° C($\alpha$).

EXAMPLE 109

Preparation of
6-1m-Nitrophenyl-imidazo[1,5-d]-as-triazin-4(3H)-one

A mixture of 90% fuming nitric acid(0.4 ml; $\alpha$=1.5, 0.0086 mole) and sulfuric acid (10 ml) is added slowly at 5° C to a solution of 6-phenyl-imidazo[1,5-d]-as triazin-4(3H)-one (2.12g, 0.01 mole) in sulfuric acid (50 ml). The mixture is stirred overnight (appr. 15–16 hours) at room temperature, and then poured over ice. The mixture is made slightly alkaline, stirred with alkyl acetate and is filtered. The isolated solid is recrystallized from aqueous dimethylformamide to yield 0.83 g of a buff-colored, fluffy solid (32%), m.p. 294°–296° C (with violent decomposition).

Analysis calculated for $C_{11}H_7N_5O_3$: C, 51.36; H, 2.74; N, 27.23; Found: C, 51.28; H, 2.85; N, 27.17.

EXAMPLE 110

Preparation of
8-Bromo-6-(m-nitrophenyl)imidazo[1,5-d]-as triazin-4(3H)-one, compound with dimethylformamide.

A mixture of 90% fuming nitric acid (1.87 ml, $\alpha$= 1.5, 0.04 mole) and sulfuric acid (10 ml) is added slowly at 5° C to a solution of 8-bromo-6-phenyl imidazo[1,5-d]-as triazine-4(3H)-one 5.82 g, 0.02 mole) in sulfuric acid. The reaction mixture is stirred for 1 hour, poured over ice, the precipitated solid is isolated by filtration and dried. A dark brown solid (6.58 g, 98%) is obtained, m.p. 244°–246° C ($\alpha$). Recrystallization from aqueous dimethyl formamide yields the title compound, a buff colored solid, m.p. 246°–248° C($\alpha$).

Analysis calculated for $C_{11}H_6BrN_5O_3$, $C_3H_7NO$: C, 41.09; H, 3.20; N, 20.54; Br, 19.53; Found C, 40.99; H, 3.15; N, 20.34, Br, 20.50.

EXAMPLE 111

Preparation of 8-Bromo-imidazo[1,5d]-as-triazin-4(3H)-one

A solution of bromine (8.0 g, 0.05 mole) in acetic acid (10 ml) is added to a mixture of imidazo[1,5-d]-as-triazine-4(3H)-one (6.8 g, 0.05 mole) and acetic acid (500 ml) The reaction mixture is stirred for 1 hour, poured into water and extracted with chloroform. The aqueous layer is separated, made slightly alkaline and extracted with ether. Evaporation of the chloroform and the ether layers yields 5.0 g of a solid (46.3%). This solid is recrystallized to afford the title product, a cream colored solid, m.p. 244°–245° C(α).

Analysis calculated for $C_5H_3BrN_4O$: C, 27.80; H, 1.40; N, 25.94; Br 37.00; Found: C, 28.99; H, 1.36; N, 26.46; Br 35.91.

EXAMPLE 112

6,8-Dibromo-imidazo[1,5-d]-as-triazin-4(3H)-one

Bromine (1.5 ml, 0.03 mole) is added dropwise to a well stirred mixture of imidazo [1,5-d]-as-triazin-4(3H)-one (1.36 g, 0.01 mole), sodium bicarbonate (2.52 g, 0.03 mole) and water (25 ml). The mixture is stirred for 4 hours and is then filtered. The isolated product is washed well with water and air-dried. The product (2.78 g, 95%) is recrystallized from toluene-hexane (1:1) to yield a cream colored solid, m.p. 210°–212° C.

Analysis calculated for $C_5H_2Br_2N_4O$: C, 20.44; H, 0.69; N, 19.10; Br 54.39; Found: C, 19.16; H, 0.88; N, 18.80; Br, 54.12.

EXAMPLE 113

Preparation of 8-bromomethyl-6-phenyl-imidazo[1,5-d]-as-triazin-4(3H)-one

A mixture of 8-methyl-6-phenylimidazo[1,1-a]-as-triazine-4(3H)-one (4.52 g, 0.02 mole), N-bromosuccinimide (3.92 g, 0.044 mole), benzoyl peroxide (0.24 g, 0.002 mole) and carbon tetrachloride (200 ml) is refluxed for 8 hours. The reaction mixture is cooled and filtered. The isolated product is washed with water and with methylene chloride. The product (2.1 g, 34.4%) is recrystallized from nitromethane to yield pale yellow crystals, m.p. 254°–256° C (d).

Analysis calculated for $C_{12}H_9BrN_4O$: C, 47.24; H, 2.97; N, 18.48; Br 26.20; Found: C, 47.50; H, 3.21; N, 18.48; Br, 25.78.

Evaporation of the filtrates and washings followed by recrystallization of the residue from nitromethane yields a second crop (14.8% of the product.

EXAMPLE 114

Preparation of 3-alkyl-8-methyl-6-phenylimidazo-as-[1,5-d]-triazin-4(3H)-ones

Method A

Sodium methoxide (0.81 g, 0.015 mole) is added to a solution of 8-methyl-6-phenylimidazo-as-[1,5-d]-triazin-4(3H)-one (3.39 g, 0.015 mole), followed by the addition of the appropriate alkylating agent (i.e. methyl iodide, allyl bromide, propargyl bromide, benzyl chloride, dipropyl sulfate, and the like). The reaction mixture is then stirred at 20° C for 16 hours, heated at 40° C for 45 minutes, cooled and poured on a mixture of ice and dilute hydrochloric acid. The product is extracted from the above aqueous mixture with chloroform and isolated by evaporation of the chloroform layer.

Purification is affected by crystallization (cyclohexane or cyclohane-benzene), or by silica gel dry column chromatography in chloroform.

Method B

3,8-Dimethyl-6-phenylimidazo[1,5-d]-as-triazin-4(3H)-one

Dimethylformamide dimethyl acetal (0.73 ml; α= 0.897, 0.005 mole) is added slowly to a slurry of 8-methyl-6-phenylimidazo[1,5-d]-as-triazin-4(3H)-one (1.13 g, 0.005 mole in benzene (25 ml). The reaction mixture is stirred, refluxed for 24 hours, cooled and filtered. The filtrate is evaporated to yield 1.4 g (100%) product. Recrystallization from methyl cyclohexane yields yellow crystals, found to be identical (ir: nmr) to the product obtained by Method A.

Compounds prepared by the above procedures are listed in Table VII below.

Table VII

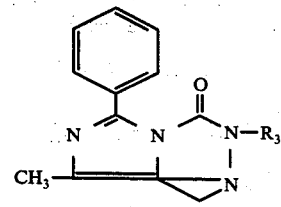

| $R_3$ | Method | m.p.(° C) | Analysis Calculated | Found |
|---|---|---|---|---|
| $CH_3$— | A or B | 144–146 | C 64.98<br>H 5.03<br>N 23.32 | C 65.09<br>H 5.11<br>N 23.45 |
| $CH_3$=CH—$CH_2$— | A | 134–134.5 | C 67.65<br>H 5.30<br>N 21.04 | C 67.70<br>H 5.25<br>N 21.21 |
| CH≡C—$CH_2$— | A | 192.5–193.5 | C 68.17<br>H 4.58<br>N 21.20 | C 68.24<br>H 4.56<br>N 21.17 |
| $C_3H_7$— | A | 144.5–145 | C 67.14<br>H 6.01<br>N 20.88 | C 67.15<br>H 6.19<br>N 20.96 |
| —$CH_2$— | A | 143–144 | C 72.13<br>H 5.10<br>N 17.71 | C 71.71<br>H 5.24<br>N 17.42 |

EXAMPLE 115

Preparation of 3,8-Dimethyl-6-phenyl-imidazo[1,5-d]-as-triazin-4(3H)-thione

8-Methyl-6-phenyl-imidazo[1,5-d]-as-triazin-4(3H)-thione (3.76 g, 0.014 mole) is dissolved in aqueous sodium bicarbonate (125 ml, 6.7%). Dimethyl sulfate (1.85 g, 0.0147 mole) is added at room temperature and the reaction mixture stirred overnight (appr. 15–16 hours). The precipitated solid is collected by filtration and washed thoroughly with water. The dried solid (3.84 g) is extracted with benzene. The benzene solution is evaporated to dryness, and the residual red solid obtained is extracted with hexane. Evaporation of the hexane solution yields a tan solid (0.25 g). Recrystallization of this tan solid from methanol yields pale yellow crystals, m.p. 194°–195° C.

Analysis calculated for $C_{13}H_{12}N_4S$: C, 60.92; H, 4.72; N, 21.86; Found: C, 60.31; H, 4.90; N, 21.34.

EXAMPLE 116

| Per Tablet | | Preparation of 50 mg. Tablets | Per 10,000 Tablets |
|---|---|---|---|
| 0.050 | gm. | 6-phenyl-8-isopropyl-imidazo[1,5-d]-as-triazine-4(3H)-thione | 500 gm. |
| 0.080 | gm. | Lactose | 800 gm. |
| 0.010 | gm. | Corn Starch (for mix) | 100 gm. |
| 0.008 | gm. | Corn Starch (for paste) | 75 gm. |
| 0.148 | gm. | | 1475 gm. |
| 0.002 | gm. | Magnesium Stearate (1%) | 15 gm. |
| 0.150 | gm. | | 1490 gm. |

The 6-phenyl-8-isopropyl-imidazo[1,5-d]-as-triazine-4(3H)-thione, lactose and corn starch (for mix) are blended together. The corn starch (for paste) is suspended in 600 ml. of water and heated with stirring to form a paste. This paste is then used to granulate the mixed powders. Additional water is used if necessary. The wet granules are passed through a No. 8 hand screen and dried at 120° F. The dry granules are then passed through a No. 16 screen. The mixture is lubricated with 1% magnesium stearate and compressed into tablets in a suitable tableting machine.

EXAMPLE 117

| Preparation of Oral Suspension | |
|---|---|
| Ingredient | Amount |
| 6-benzyl-8-ethyl-imidazo[1,5-d]-as-triazin-4(3H)-one | 500 mg. |
| Sorbitol solution (70% N.F.) | 40 ml. |
| Sodium benzoate | 150 mg. |
| Saccharin | 10 mg. |
| Red dye | 10 mg. |
| Cherry flavor | 50 mg. |
| Distilled water qs to | 100 ml. |

The orbitol solution is added to 40 ml. of distilled water and the 6-benzyl-8-ethyl-imidazo[1,5-d]-as-triazin-4(3H)-one is suspended therein. The saccharin, sodium benzoate, flavor and dye are added and dissolved. The volume is adjusted to 100 ml. with distilled water. Each ml. of syrup contains 5 mg. of 6-benzyl-8-ethyl-imidazo-[1,5-d]-as-triazin-4(3H)-one.

EXAMPLE 118

Preparation of Parenteral Solution

In a solution of 700 ml. of propylene glycol and 200 ml. of water for injection is suspended 20.0 grams of 6-isobutyl-8-n-propyl-imidazo[1,5-d]-as-triazin-4(3H)-one with stirring. After suspension is complete, the pH is adjusted to 5.5 with hydrochloric acid and the volume is made up to 1000 ml. with water for injection. The formulation is sterilized, filled into 5.0 ml. ampoules each containing 2.0 ml. (representing 40 mg. of drug) and sealed under nitrogen.

EXAMPLE 119

Preparation of Aerosol Spray

A suspension is prepared of:

| | |
|---|---|
| 8-chloro-6-isopropyl-imidazo[1,5-d]-as-triazine-4(3H)-thione; micronized (0.5–5.0 microns) | 400 mg. |
| Dichlorodifluoromethane | 100 ml. |
| Sorbitan trioleate | 6.9 mg. |

The active ingredient and sorbitan trioleate are placed in a beaker and the dichlorodifluoromethane is added at −40° C. whereupon a suspension is formed. The mixture is sonified, that is, treated with a Sonifier, manufactured by the Branson Sonic Power Co. of Danbury, Conn., as model LS-75 at a current input of 9 amperes for 2 minutes. Additional cold dichlorodifluoromethane is added as necessary to keep the volume at 100 ml. The mixture is uniformly dispersed, and has increased stability resulting from the sonification. Each of six 19 ml. stainless steel containers are filled with 15 ml. of the cold mixture, then valves are inserted and sealed in place. On warming, after storage, the 8-chloro-6-isopropyl-imidazo[1,5-d]-as-triazine-4(3H)-thione remains dispersed and, after merely casual shaking gives uniform doses of finely divided drug.

We claim:

1. A compound of the formula:

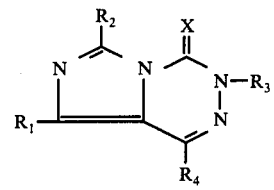

wherein X is divalent oxygen or divalent sulfur; $R_1$ is selected from the group consisting of hydrogen, alkyl $(C_1-C_3)$, chloro, bromo, iodo and haloalkyl $(C_1-C_3)$; $R_2$ is selected from the group consisting of hydrogen, alkyl $(C_1-C_4)$, cycloalkyl $(C_3-C_6)$, methoxymethyl, benzyl, naphthyl, phenyl and mono-substituted phenyl wherein said substituent is selected from the group consisting of halo, alkyl $(C_1-C_4)$, haloalkyl $(C_1-C_3)$ amino, dialkylamino and nitro; $R_3$ is selected from the group consisting of hydrogen, alkyl $(C_1-C_3)$, alkenyl $(C_3-C_4)$ and alkynyl $(C_3-C_4)$; $R_4$ is selected from the group consisting of hydrogen and alkyl $(C_1-C_3)$.

2. The compound according to claim 1 wherein X is oxygen; $R_1$ is methyl, bromo or chloro; $R_2$ is cycloalkyl $(C_3-C_6)$, phenyl or m-tolyl; and $R_3$ and $R_4$ are both hydrogen.

3. The compound according to claim 1 wherein X is oxygen and $R_1$ and $R_2$ are both hydrogen.

4. The compound according to claim 1 wherein X is sulfur and $R_1$ and $R_2$ are both hydrogen.

5. The compound according to claim 1 wherein X is oxygen, $R_1$ is methyl, and $R_2$ is phenyl.

6. The compound according to claim 1 wherein X is sulfur, $R_1$ is methyl, and $R_2$ is phenyl.

7. The compound according to claim 1 wherein X is oxygen and $R_1$ and $R_2$ are both methyl.

8. The compound according to claim 1 wherein X is sulfur and $R_1$ and $R_2$ are both methyl.

9. The compound according to claim 1 wherein X is oxygen, $R_1$ is bromo, and $R_2$ is phenyl.

10. The compound according to claim 1 wherein X is sulfur, $R_1$ is methyl, and $R_2$ is benzyl.

11. The compound according to claim 1 wherein X is oxygen, $R_1$ is chloro and $R_2$ is phenyl.

12. The compound according to claim 1 wherein X is oxygen, $R_1$ and $R_3$ are both methyl, and $R_2$ is phenyl.

13. The compound according to claim 1 wherein X is oxygen, $R_1$ is methyl and $R_2$ is n-propyl.

14. The compound according to claim 1 wherein X is oxygen, $R_1$ is methyl, and $R_2$ is tert-butyl.

15. The compound according to claim 1 wherein X is oxygen, $R_1$ is chloro, and $R_2$ is p-chlorophenyl.

16. The compound according to claim 1 wherein X is oxygen, $R_1$ is methyl, and $R_2$ is cyclohexyl.

17. The compound according to claim 1 wherein X is oxygen, $R_1$ is methyl, and $R_2$ is m-tolyl.

18. The compound according to claim 1 wherein X is oxygen, $R_1$ is iodo, and $R_2$ is phenyl.

19. The compound according to claim 1 wherein X is oxygen, $R_1$ is methyl and $R_2$ is p-aminophenyl.

20. The compound according to claim 1 wherein X is oxygen, $R_1$ is bromo, and $R_2$ is m-dimethylaminophenyl.

21. The compound according to claim 1 wherein $R_1$ is methyl and $R_2$ is 2-naphthyl.

22. A method of inhibiting the enzyme phosphodiesterase in a mammal which comprises administering internally to said mammal an effective amount of a compound of the formula:

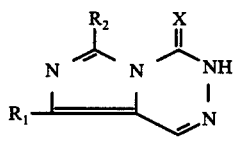

wherein X is divalent oxygen or divalent sulfur; $R_1$ is selected from the group consisting of hydrogen, chloro, bromo and alkyl having up to 3 carbon atoms; and $R_2$ is selected from the group consisting of hydrogen, alkyl having up to 4 carbon atoms, phenyl, benzyl, methoxymethyl and o-propoxyphenyl.

23. A therapeutic composition in dosage unit form useful for inhibiting the enzyme phosphodisterase in mammals comprising from about 1.0 mg. to about 25.0 mg. per kg. of body weight per daily dosage unit, in association with a pharmaceutical carrier, of a compound of that formula:

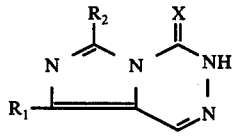

wherein X is divalent oxygen or divalent sulfur; $R_1$ is selected from the group consisting of hydrogen, chloro, bromo and alkyl having up to 3 carbon atoms, and $R_2$ is selected from the group consisting of hydrogen, alkyl having up to 4 carbon atoms, phenyl, benzyl, methoxymethyl and o-propoxyphenyl.

24. The process of preparing compounds of the formula:

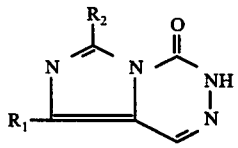

wherein $R_1$ is hydrogen or alkyl having up to 3 carbon atoms and $R_2$ is hydrogen, alkyl having up to 4 carbon atoms, phenyl, benzyl, methoxymethyl or o-propoxyphenyl which comprises heating a compound of the formula:

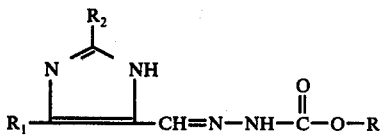

wherein R is methyl or ethyl and $R_1$ and $R_2$ are as hereinabove defined in a non-polar high boiling organic solvent at a temperature of 175°–275° C. for a period of time sufficient for a substantial degree of ring closure to occur.

25. The process of preparing compounds of the formula:

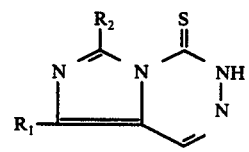

wherein $R_1$ is hydrogen or alkyl having up to 3 carbon atoms and $R_2$ is hydrogen, alkyl having up to 4 carbon atoms, phenyl, benzyl, methoxymethyl or o-propoxypheyl which comprises heating a compound of the formula:

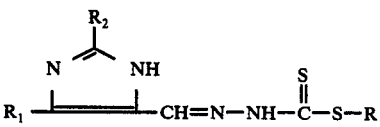

wherein R is methyl or ethyl and $R_1$ and $R_2$ are as hereinabove defined in a non-polar high boiling organic solvent at a temperature of 175°–275° C. for a period of time sufficient for a substantial degree of ring closure to occur.

26. The process of preparing compounds of the formula:

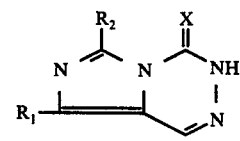

wherein X is divalent oxygen or divalent sulfur; $R_1$ is chloro or bromo; and $R_2$ is hydrogen, alkyl having up to 4 carbon atoms, phenyl, benzyl, methoxymethyl or o-propoxyphenyl which comprises treating a compound of the formula:

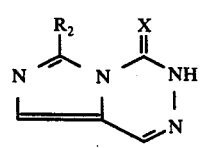

wherein X and $R_2$ are as hereinabove defined with chlorine or bromine in an inert solvent at a temperature of 60°–90° C. for a period of time sufficient for a substantial degree of halogenation to occur.

27. The process of preparing compounds of the formula:

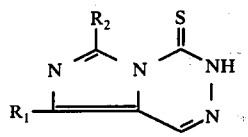

wherein $R_1$ is hydrogren, chloro, bromo or alkyl having up to 3 carbon atoms and $R_2$ is hydrogen, alkyl having up to 4 carbon atoms, phenyl, benzyl, methoxymethyl or o-propoxyphenyl which comprises treating a compound of the formula:

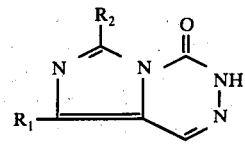

wherein $R_1$ and $R_2$ are as hereinabove defined with phosphorus pentasulfide in an inert solvent at a temperature of 100°–150° C. for a period of time sufficient for a substantial degree of replacement to occur.

* * * * *